United States Patent
Yum et al.

(10) Patent No.: US 11,612,650 B2
(45) Date of Patent: Mar. 28, 2023

(54) VACCINE ADJUVANT COMPRISING LIPOPEPTIDE-INSERTED LIPOSOME AS EFFECTIVE INGREDIENT AND USE THEREOF

(71) Applicant: CHA VACCINE RESEARCH INSTITUTE CO., LTD, Gyeonggi-do (KR)

(72) Inventors: Jung Sun Yum, Gyeonggi-do (KR);
Byung Cheol Ahn, Gyeonggi-do (KR);
Hyun Jin Jo, Gyeonggi-do (KR);
Seung Hee Baek, Gyeonggi-do (KR);
Eun Jung Jung, Gyeonggi-do (KR);
Sookyung Jeong, Gyeonggi-do (KR)

(73) Assignee: CHA VACCINE RESEARCH INSTITUTE CO., LTD, Gyeonggi-Do (KR)

( * ) Notice: Subject to any disclaimer, the term of this patent is extended or adjusted under 35 U.S.C. 154(b) by 0 days.

(21) Appl. No.: 16/639,302

(22) PCT Filed: Aug. 10, 2018

(86) PCT No.: PCT/KR2018/009173
§ 371 (c)(1),
(2) Date: Feb. 14, 2020

(87) PCT Pub. No.: WO2019/035605
PCT Pub. Date: Feb. 21, 2019

(65) Prior Publication Data
US 2020/0261567 A1    Aug. 20, 2020

(30) Foreign Application Priority Data

Aug. 16, 2017  (KR) .................. 10-2017-0103788
Jan. 16, 2018  (KR) .................. 10-2018-0005418

(51) Int. Cl.
| | |
|---|---|
| A61K 39/25 | (2006.01) |
| A61P 31/22 | (2006.01) |
| A61P 31/16 | (2006.01) |
| A61K 9/127 | (2006.01) |
| A61K 39/145 | (2006.01) |
| A61K 39/39 | (2006.01) |
| A61K 39/00 | (2006.01) |

(52) U.S. Cl.
CPC .............. *A61K 39/25* (2013.01); *A61K 9/127* (2013.01); *A61K 39/145* (2013.01); *A61K 39/39* (2013.01); *A61P 31/16* (2018.01); *A61P 31/22* (2018.01); *A61K 2039/55516* (2013.01); *A61K 2039/55561* (2013.01)

(58) Field of Classification Search
None
See application file for complete search history.

(56) References Cited

U.S. PATENT DOCUMENTS

| | | |
|---|---|---|
| 2007/0298093 A1 | 12/2007 | Konur et al. |
| 2015/0064240 A1 | 3/2015 | Peterson et al. |
| 2016/0256542 A1 | 9/2016 | Guzman |

FOREIGN PATENT DOCUMENTS

| | | | |
|---|---|---|---|
| JP | 2011-506309 A | | 3/2011 |
| JP | 2014-528955 A | | 10/2014 |
| KR | 10-1501583 B1 | | 3/2015 |
| KR | 10-2016-0007640 A | | 1/2016 |
| WO | 2009/072767 A2 | | 6/2009 |
| WO | 2013/049941 A1 | | 4/2013 |
| WO | WO/17/083963 | * | 5/2017 |

OTHER PUBLICATIONS

Fochesato et al., Short Report Comparative preclinical evaluation of AS01 versus other Adjuvant Systems in a candidate herpes zoster glycoprotein E subunit vaccine, 2016, Human Vaccines and Immunotherapeutics, vol. 12, No. 8, pp. 2092-2095.*
Suzanne M. Bal, Co-encapsulation of antigen and Toll-like receptor ligand in cationic liposomes affects the quality of the immune response in mice after intradermal vaccination, Vaccine 29 (2011) 1045-1052.
Isabelle Fernandes et al., Synthetic Lipopeptides Incorporated in Liposomes: In Vitro Stimulation of the Proliferation of Murine Splenocytes and In Vw0 Induction of an Immune Response Against a Peptide Antigen, Molecular Immunology, vol. 34, No. 819. pp. 569-576. 1997.
International Search Report issued in PCT/KR2018/009173 dated Mar. 8, 2019.
"Boeckler el al., "Design and Synthesis of Thiol-Reactive Lipopeptides" Bioorg Med Chem Lett. Aug. 4, 1998;8(15):2055-8".
Heurtault el al., "Liposome-based Systems for Anti-tumor Vaccination: Influence of Lipopetide Adjuvants" J Liposome Res. 2006;16(3):205-13.
Ingale el al., "Synthesis of Glyco(lipo) peptides by Liposome-Mediated Native Chemical Ligation" Org. Lett., vol. 8, Issue 25, 2006, pp. 5785-5788.
Lee et al., "Combination of TLR1/2 and TLR3 ligands enhances CD4+ T Cell longevity and antibody responses by modulating type IIFN production" sci. rep., vol. 6, Article No. 32526, 2016.

(Continued)

*Primary Examiner* — Benjamin P Blumel
(74) *Attorney, Agent, or Firm* — Workman Nydegger

(57) ABSTRACT

The present invention relates to a recombinant herpes zoster vaccine comprising liposome and lipopeptide and a method for preparing the same. More particularly, a vaccine composition according to the present invention, prepared using Lipo-Pam, which is a composite adjuvant comprising a liposome and various kinds of lipopeptides, and a varicella-zoster virus gE antigen, a Japanese encephalitis virus gE antigen, or a seasonal inactivated influenza virus antigen, highly induces a cell-mediated immune response as well as a humoral immune response so that the composition of the present invention can be commercially useful.

20 Claims, 44 Drawing Sheets

Specification includes a Sequence Listing.

(56) References Cited

OTHER PUBLICATIONS

Schmidt et al., "Liposome-Based Adjuvants for Subunit Vaccines: Formulation Strategies for Subunit Antigens and Immunostimulators" Pharmaceutics. Mar. 2016; 8(1): 7.
Uchida et al., "Application of Surface-Linked Liposomal anitgens to the Development of Vaccines That Induce Both Humoral and Cellular Immunity" Jpn J Infect Dis. 2014; 67(4):235-44.
Béatrice Heurtault et al: "Liposome-based systems for anti-tumor vaccination: influence of lipopeptide adjuvants", Journal of Liposome Research, Taylor & Francis, Philadelphia, PA, US, vol. 16, No. 3, Sep. 1, 2006 (Sep. 1, 2006), pp. 205-213, XP008173217.
Boeckler C et al: "Design and Synthesis of Thiol-Reactive Lipopeptides", Biorganic & Medicinal Chemistry Letters, Elsevier, Amsterdam, NL, vol. 8, No. 15, Aug. 4, 1998 (Aug. 4, 1998), pp. 2055-2058, XP004137185.
Ingale Sampat et al: "Synthesis of glyco(lipo)peptides by liposome-mediated native chemical ligation", Organic Letters, American Chemical Society, US, vol. 8, No. 25, Dec. 7, 2006(Dec. 7, 2006), pp. 5785-5788, XP002468907.
Jpn J Infect Dis.,2014,67, p. 235-244.
Lee Bo Ryeong et al: "Combination of TLR1/2 and TLR3 ligands enhances CD4(+) T cell longevity and antibody responses by modulating type I IFN production", Scientific Reports, vol. 6, Sep. 1, 2016 (Sep. 1, 2016), XP009526811.
Pharmaceutics,2016,8,7,p. 1-22.
Vaccine, 2011, 29, p. 1045-1052.

\* cited by examiner

[Fig. 1]
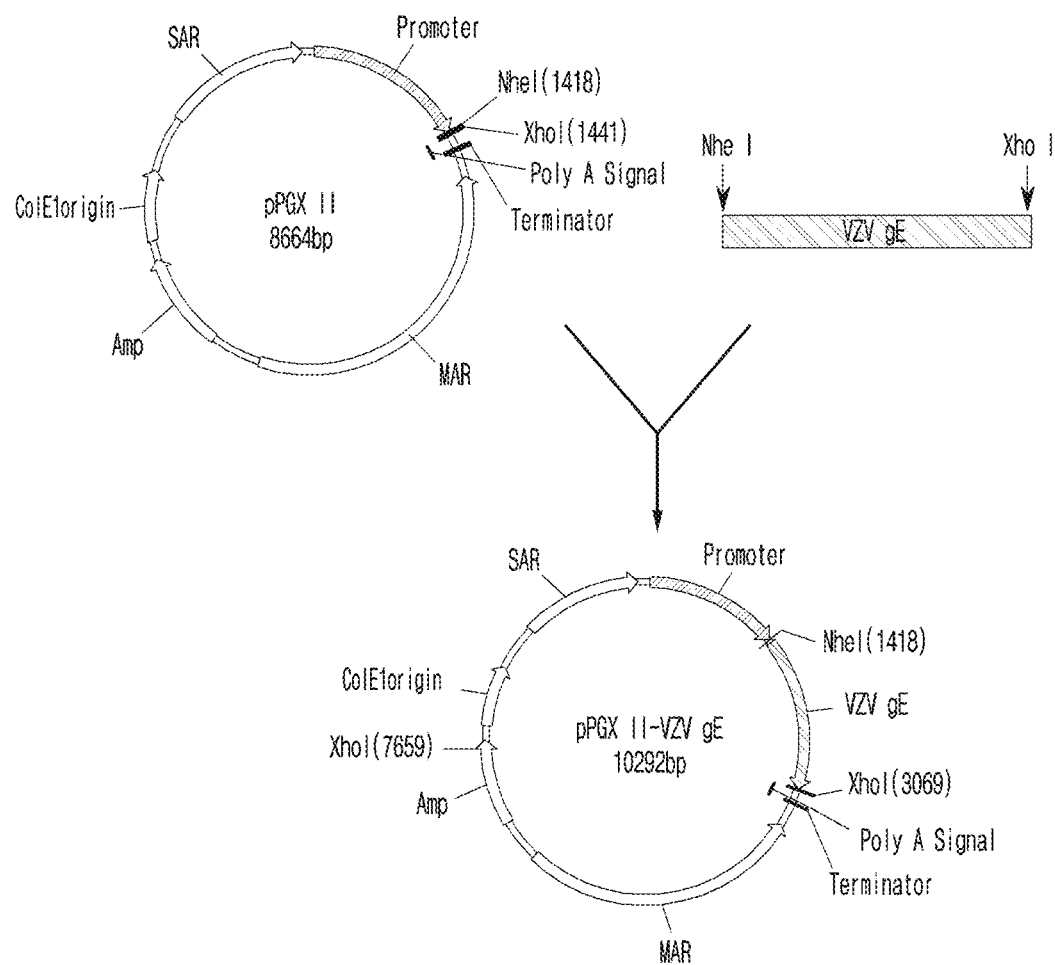

[Fig. 2a]
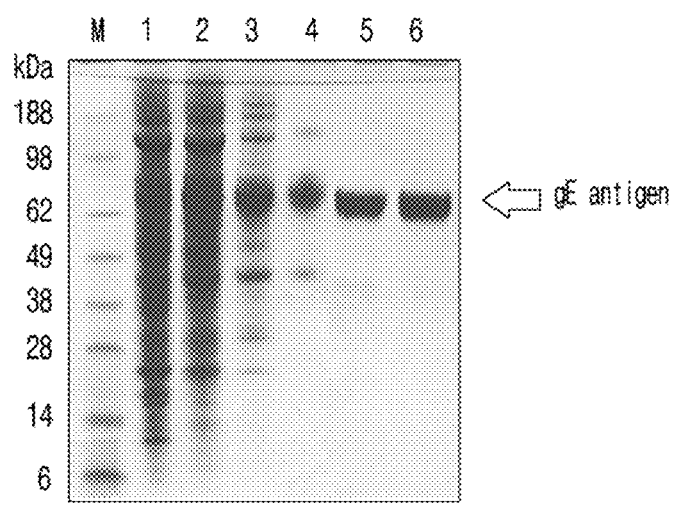

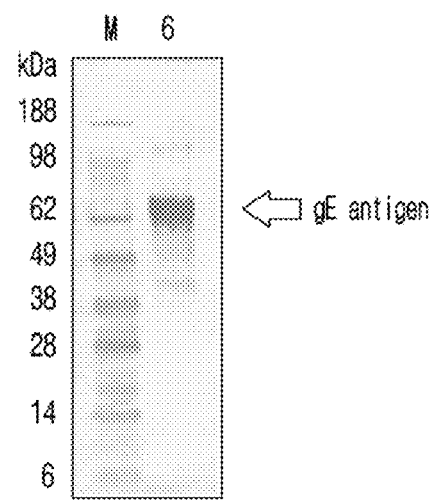
[Fig. 2b]

[Fig. 3a]
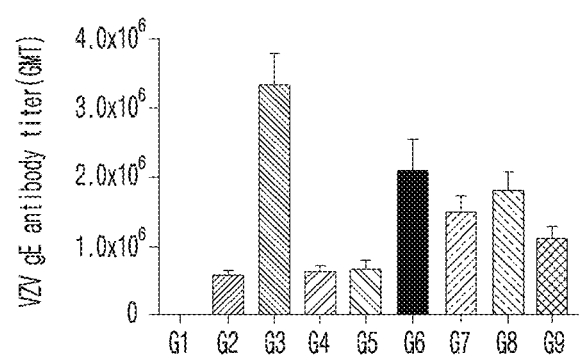

[Fig. 3b]
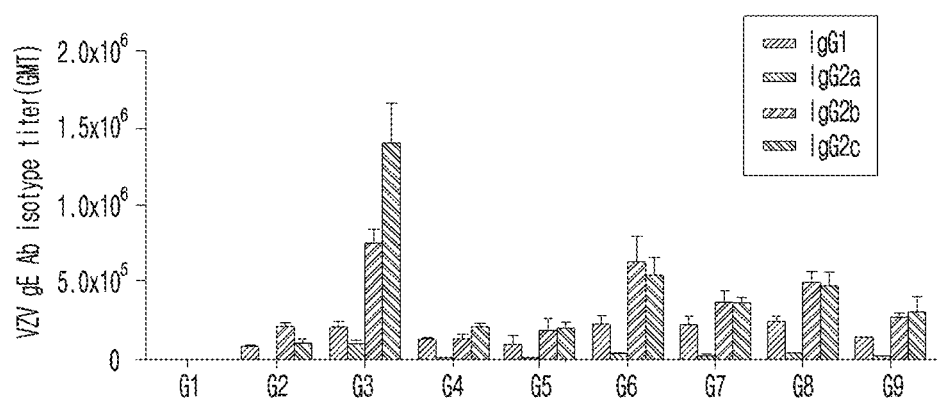

[Fig. 4a]
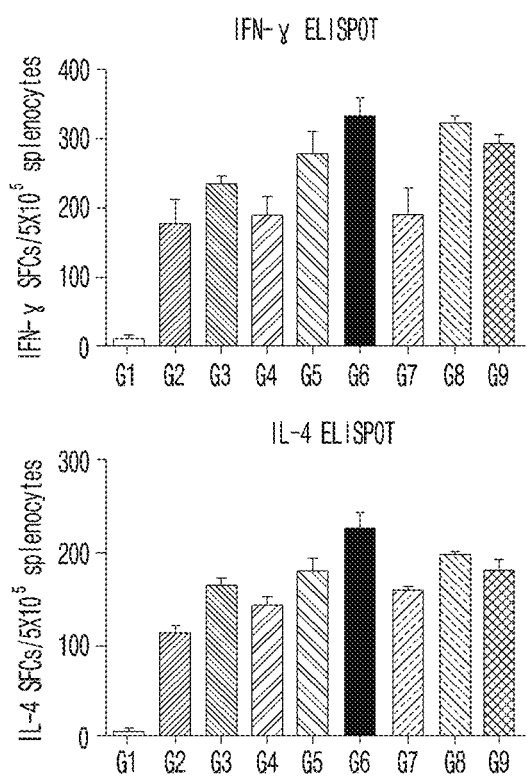

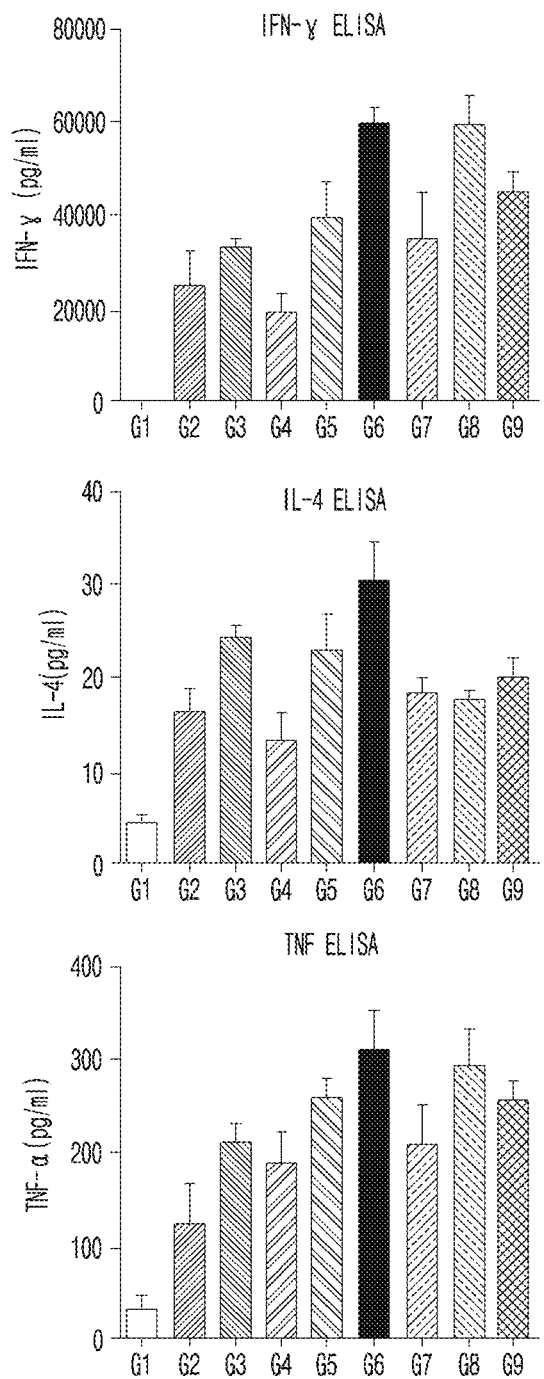
[Fig. 4b]

[Fig. 5]
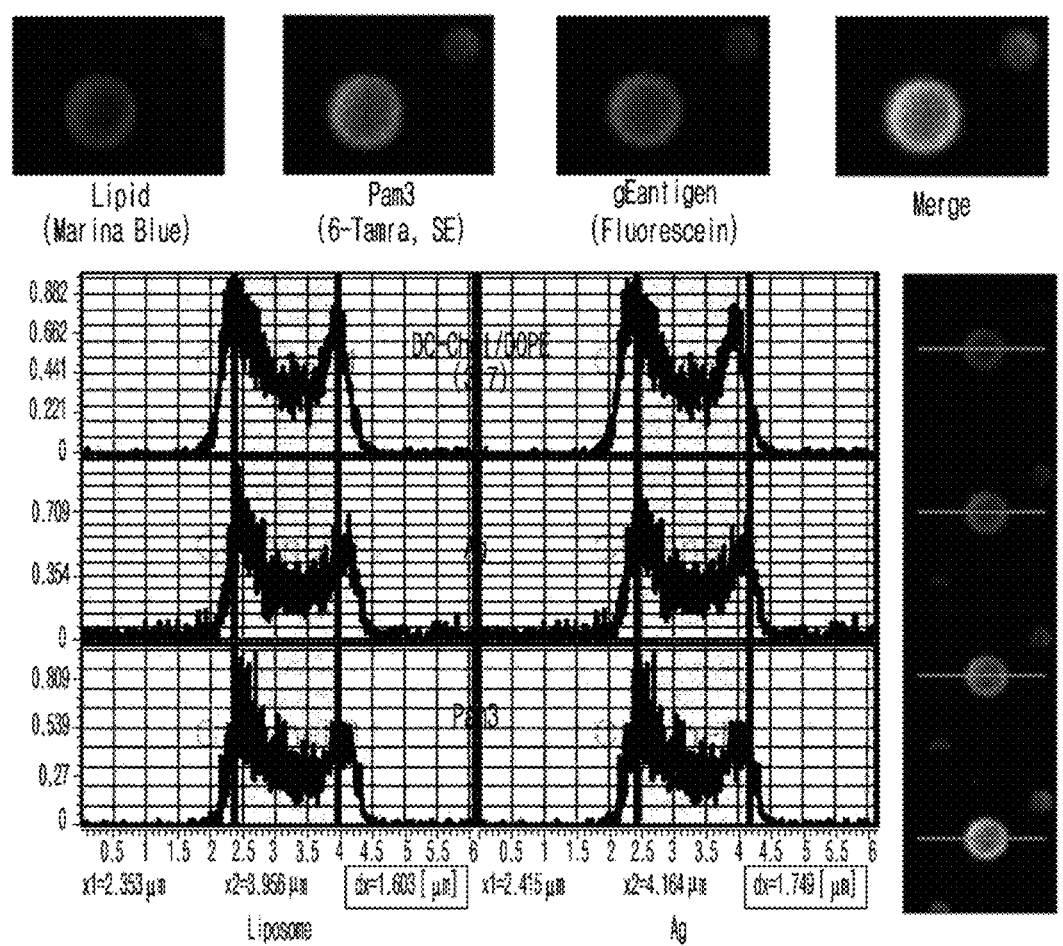

[Fig. 6]
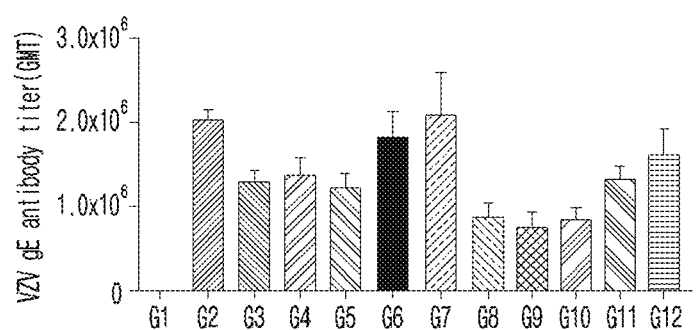

[Fig. 7a]
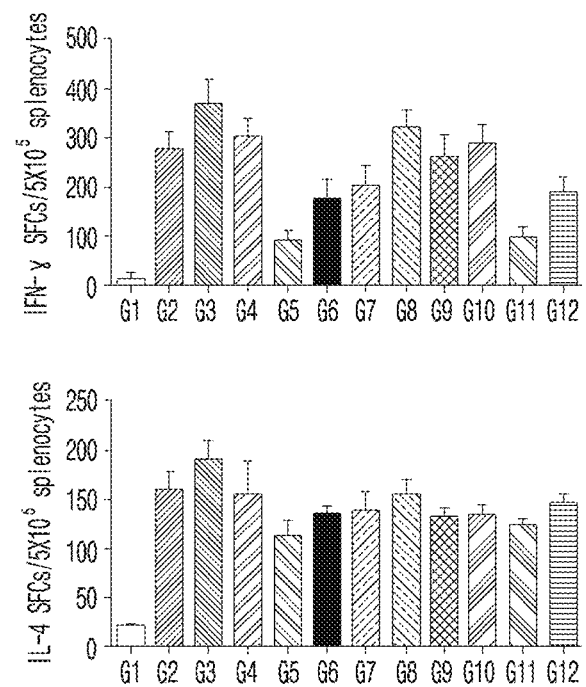

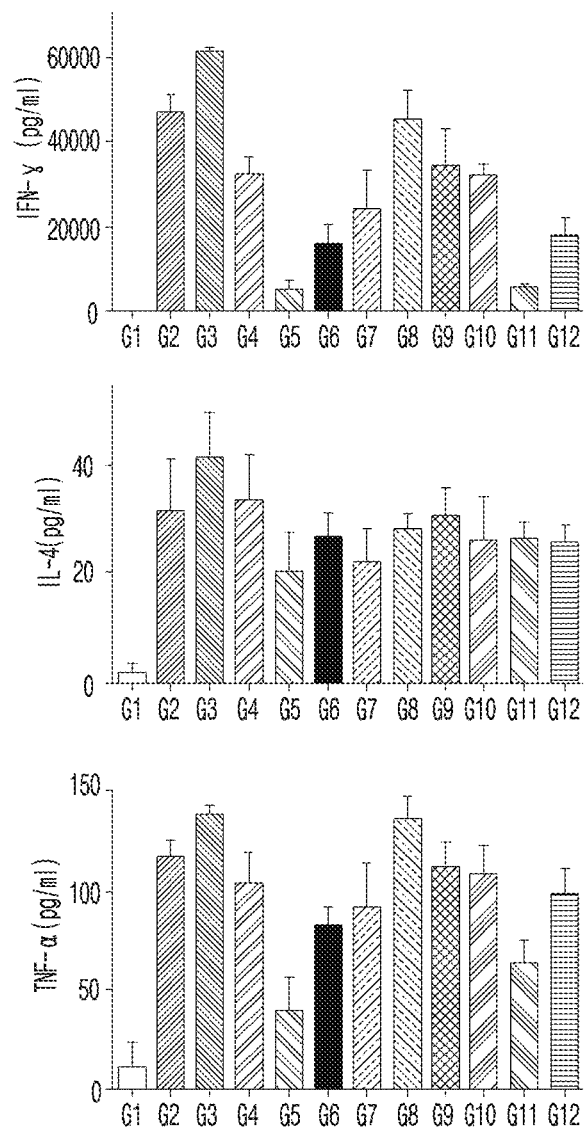
[Fig. 7b]

[Fig. 8]
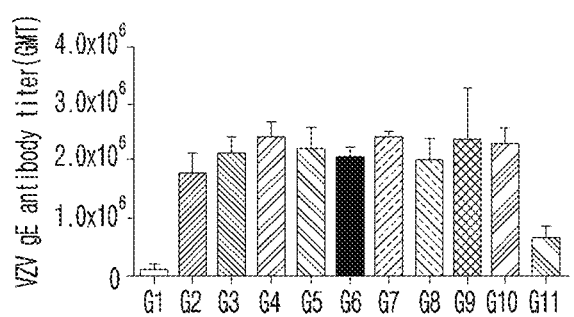

[Fig. 9a]
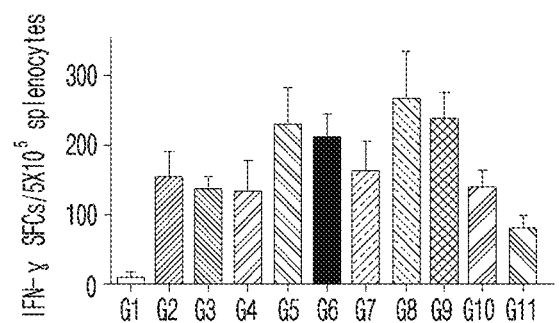
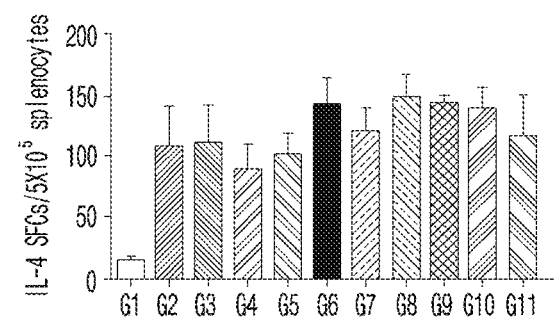

[Fig. 9b]
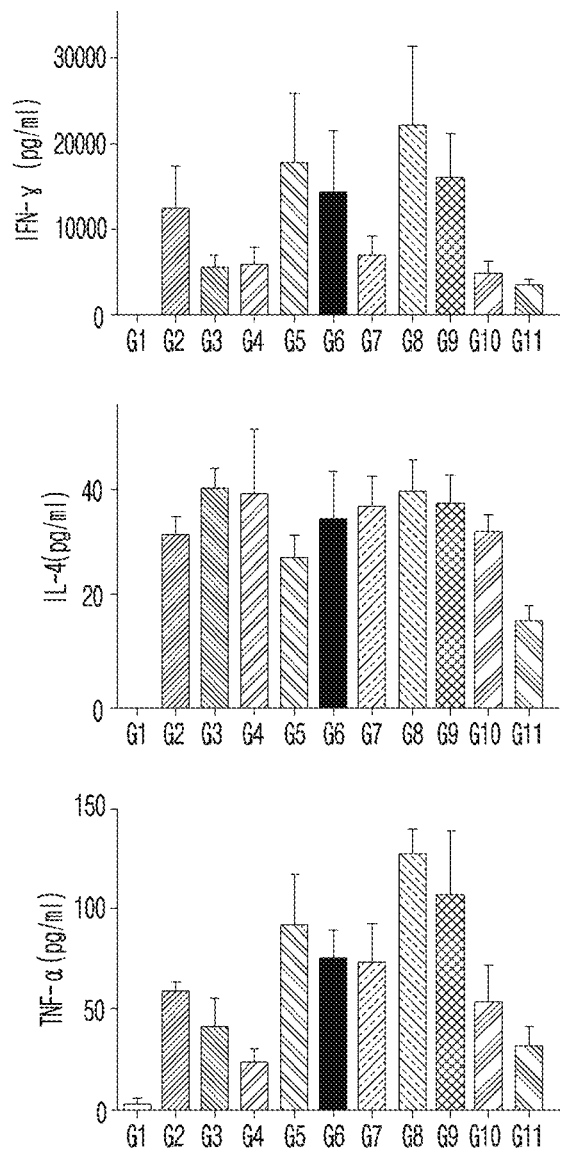

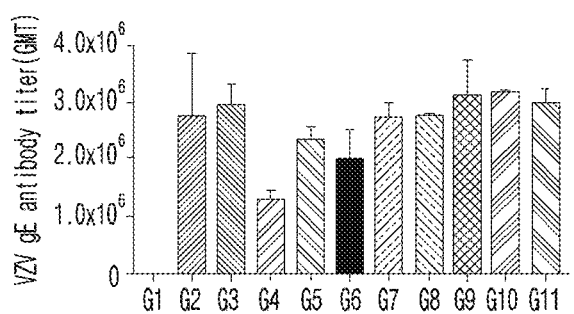
[Fig. 10]

[Fig. 11a]
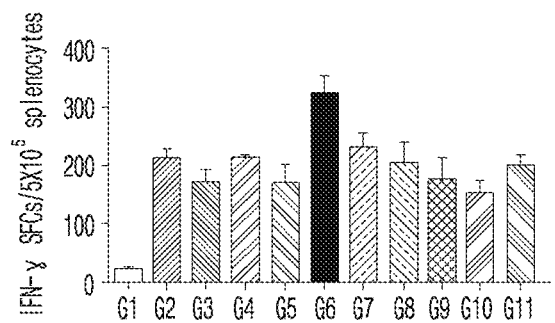
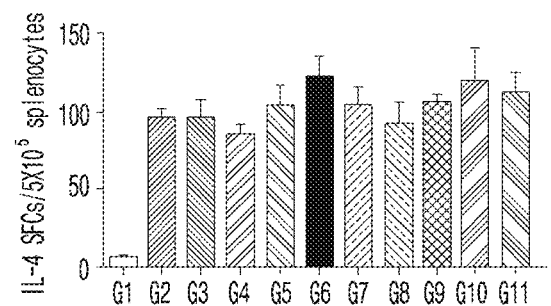

[Fig. 11b]
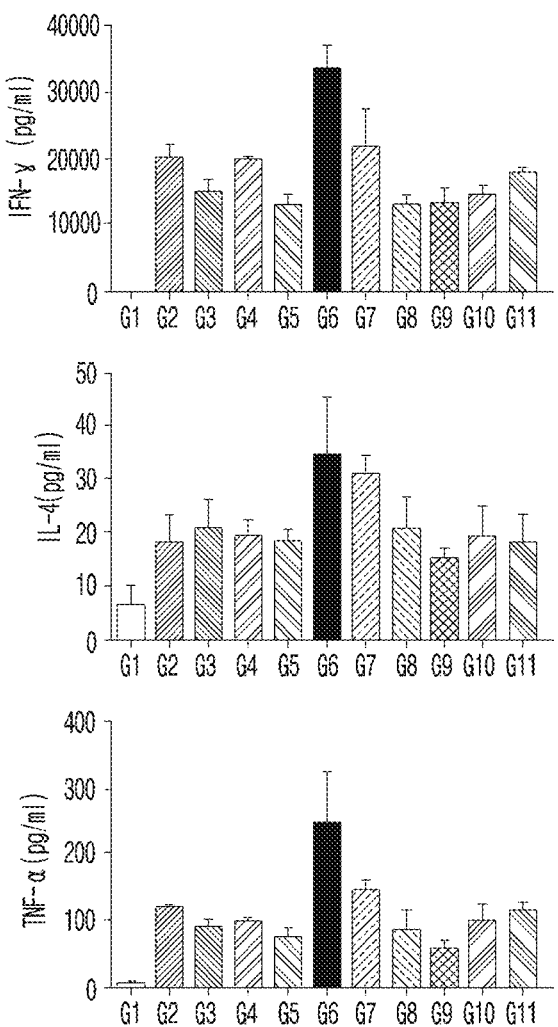

[Fig. 12]
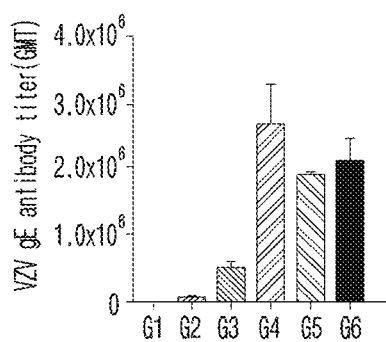

[Fig. 13a]
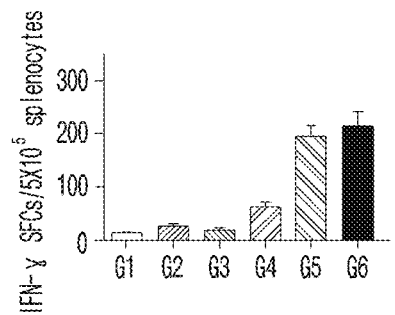
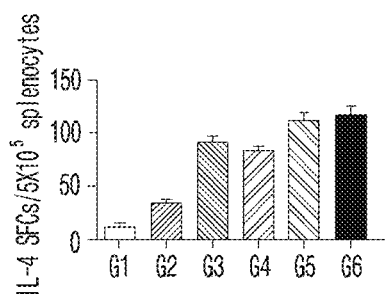

[Fig. 13b]
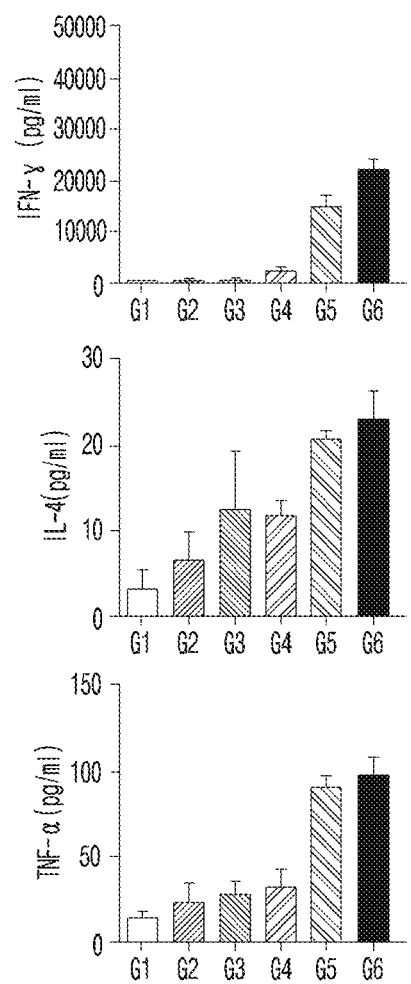

[Fig. 14]
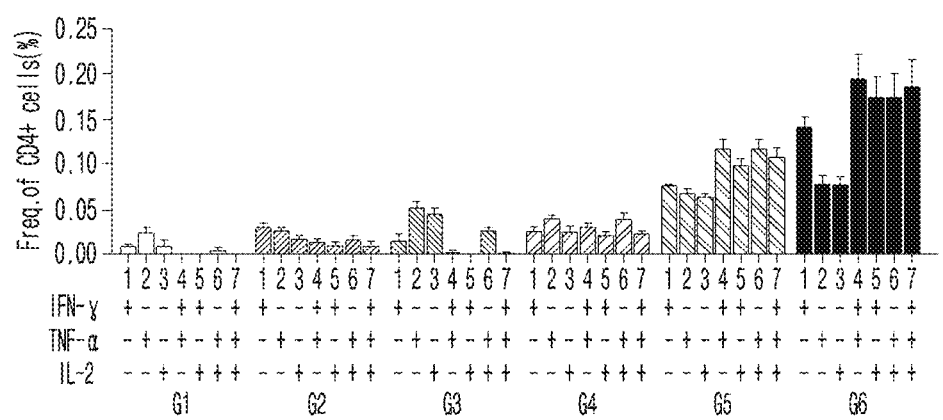

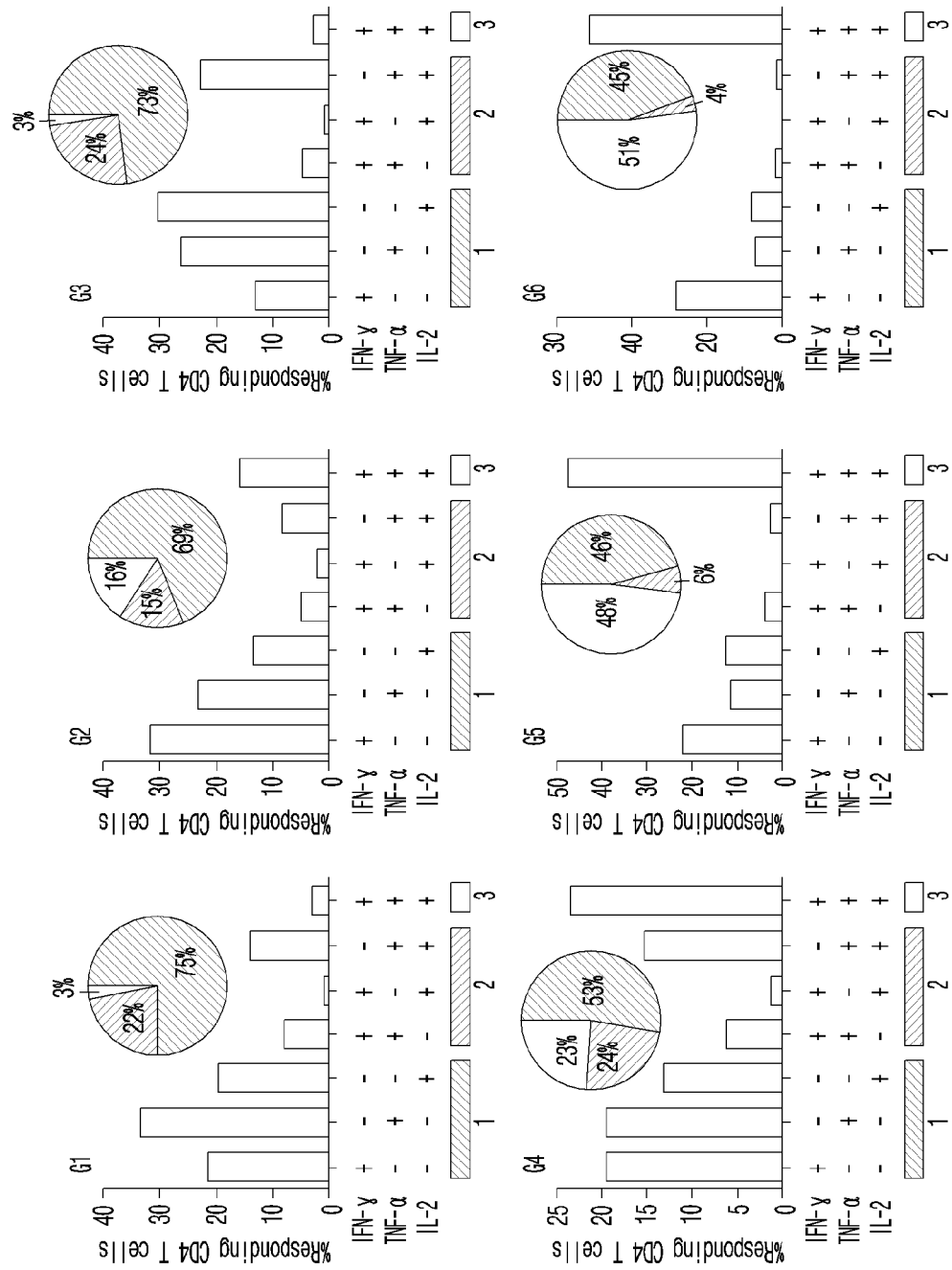
[Fig. 15]

[Fig. 16]
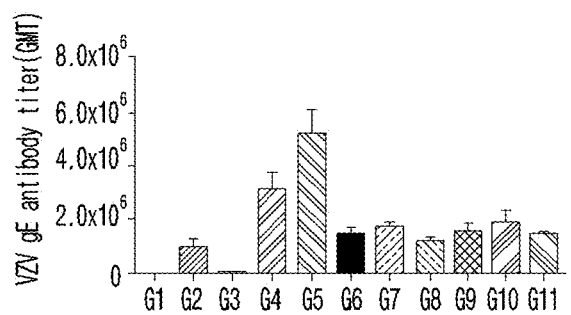

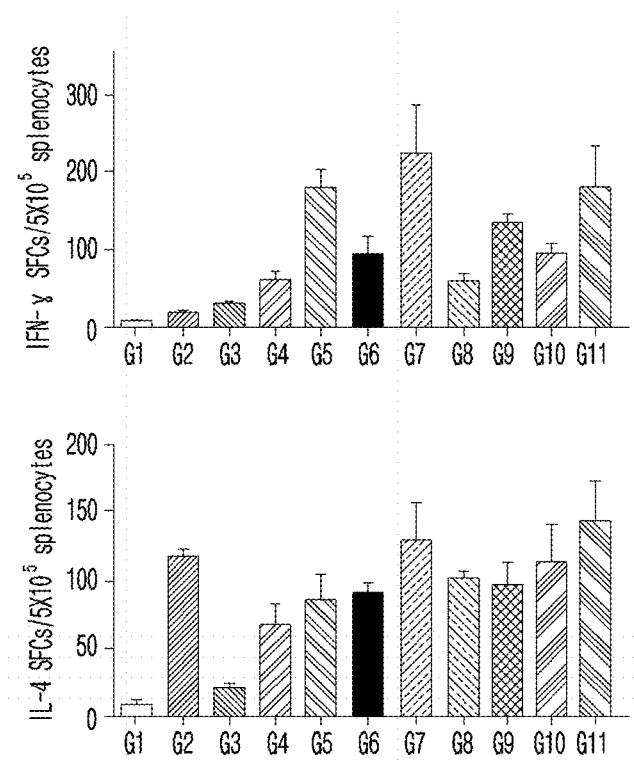
[Fig. 17a]

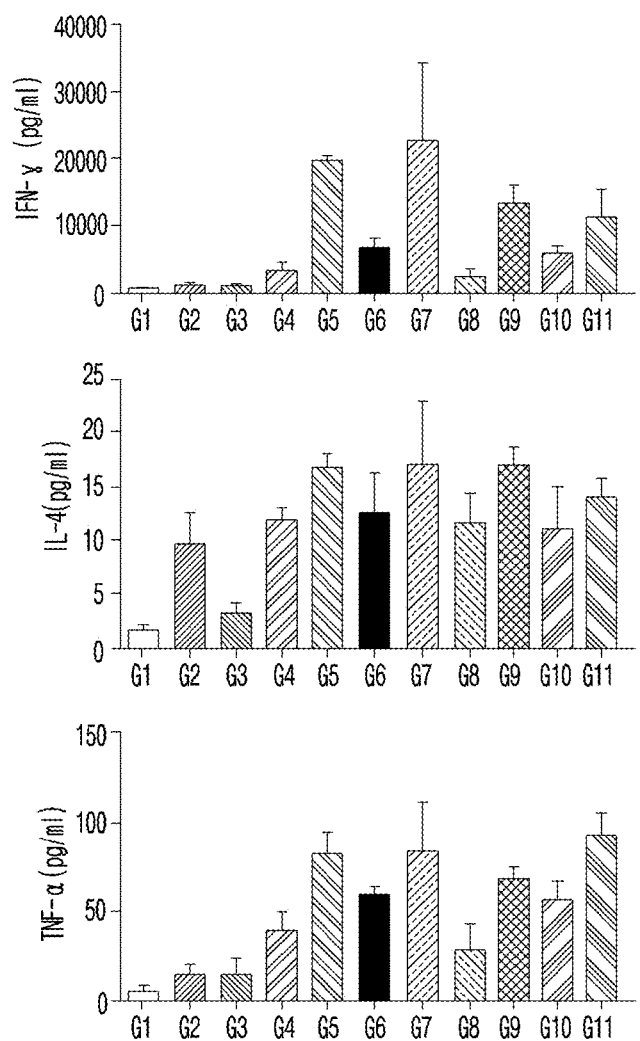
[Fig. 17b]

[Fig. 18]
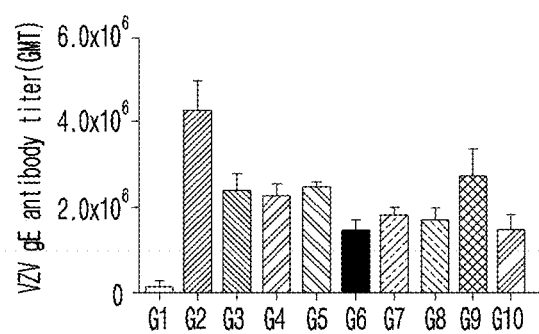

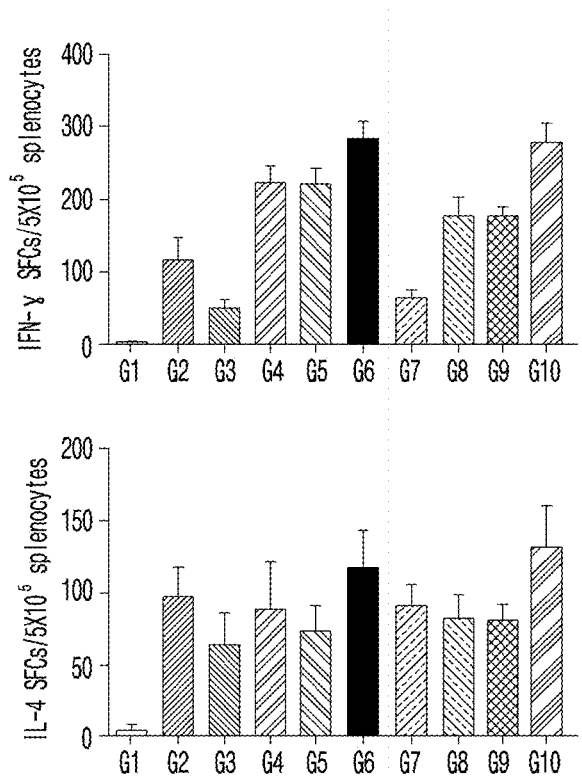
[Fig. 19a]

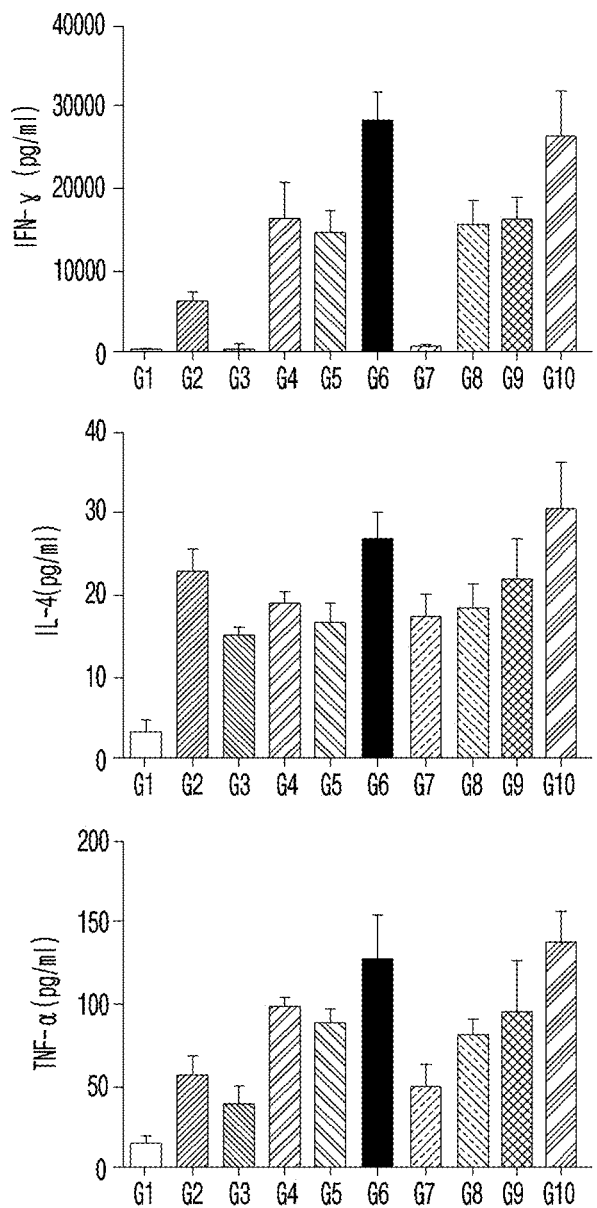
[Fig. 19b]

[Fig. 20]
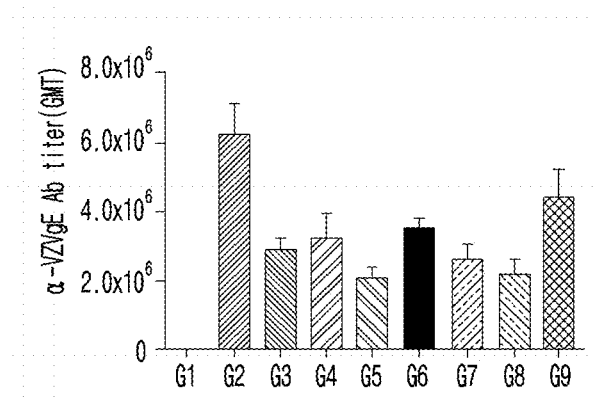

[Fig. 21a]
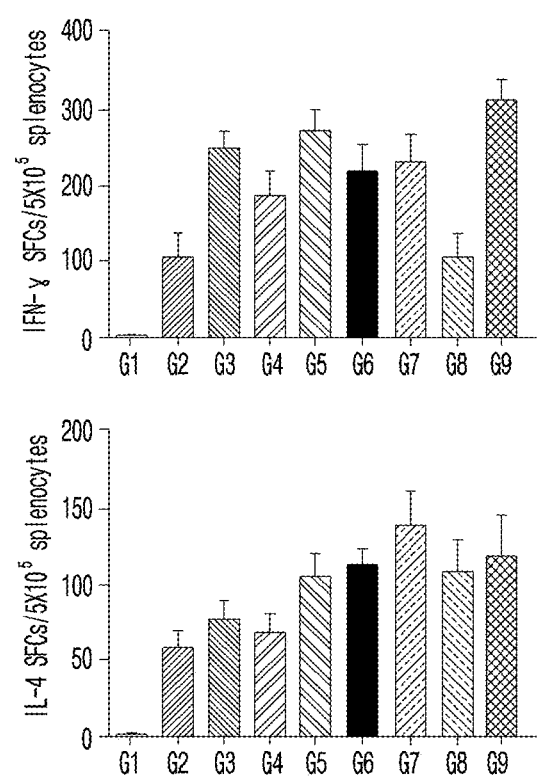

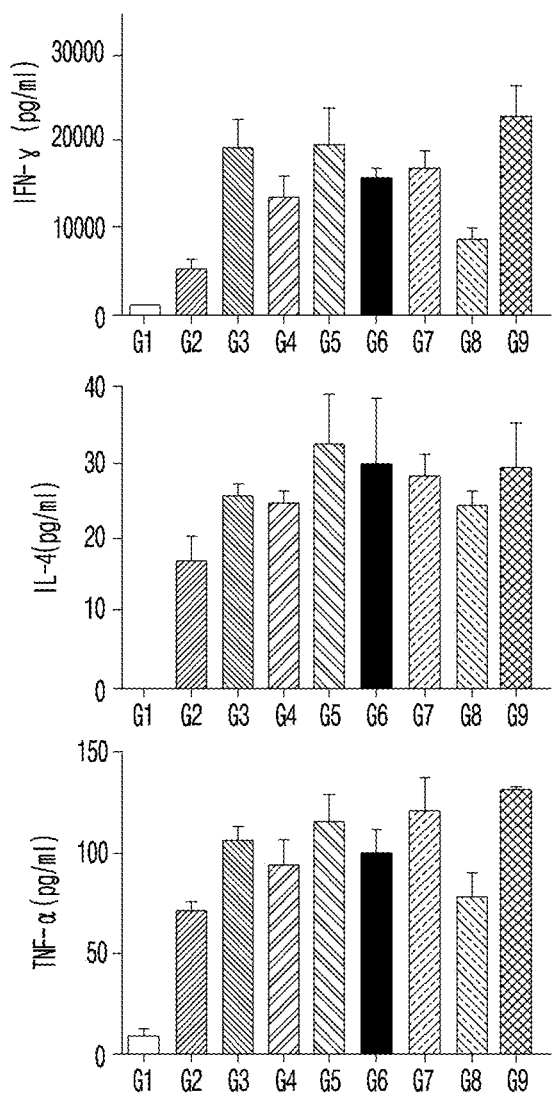
[Fig. 21b]

[Fig. 22]
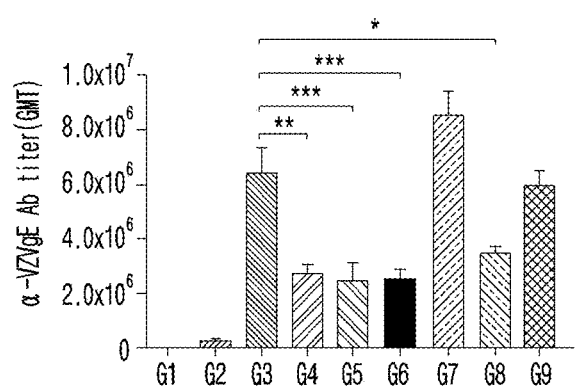

[Fig. 23a]
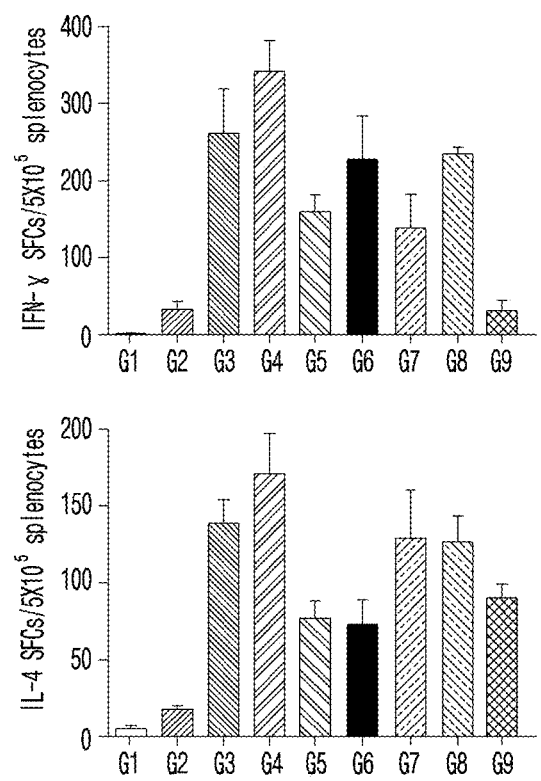

[Fig. 23b]
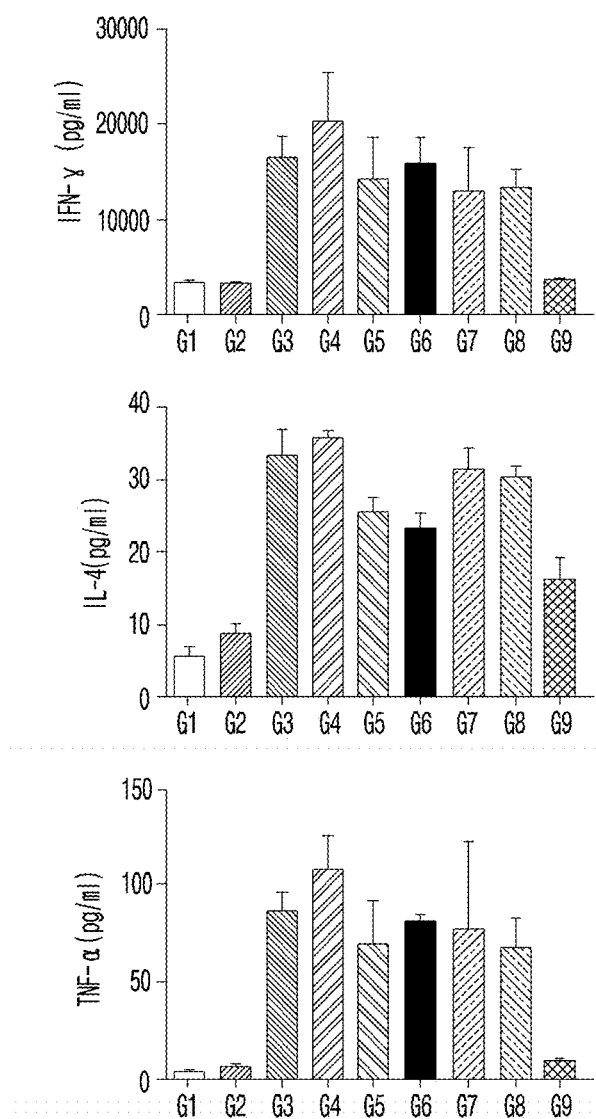

[Fig. 24a]
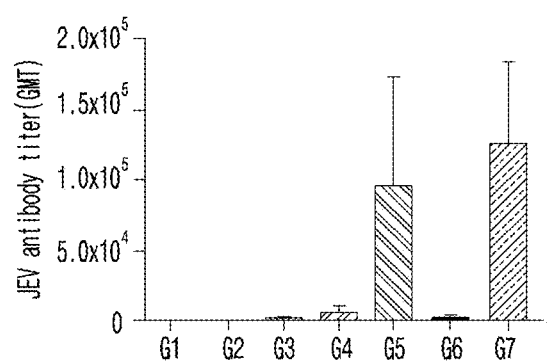

[Fig. 24b]
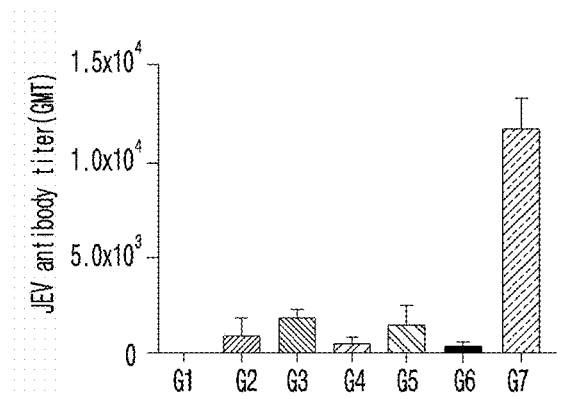

[Fig. 25a]
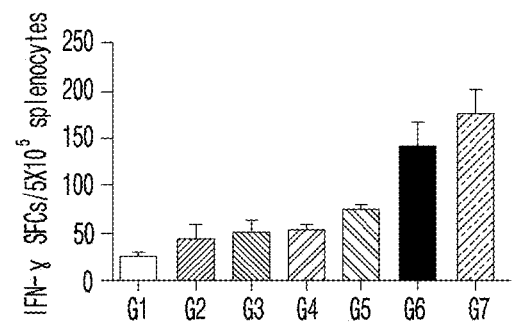
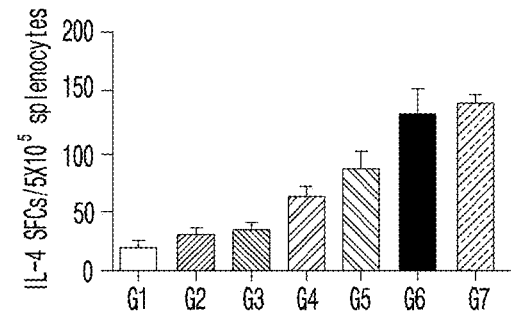

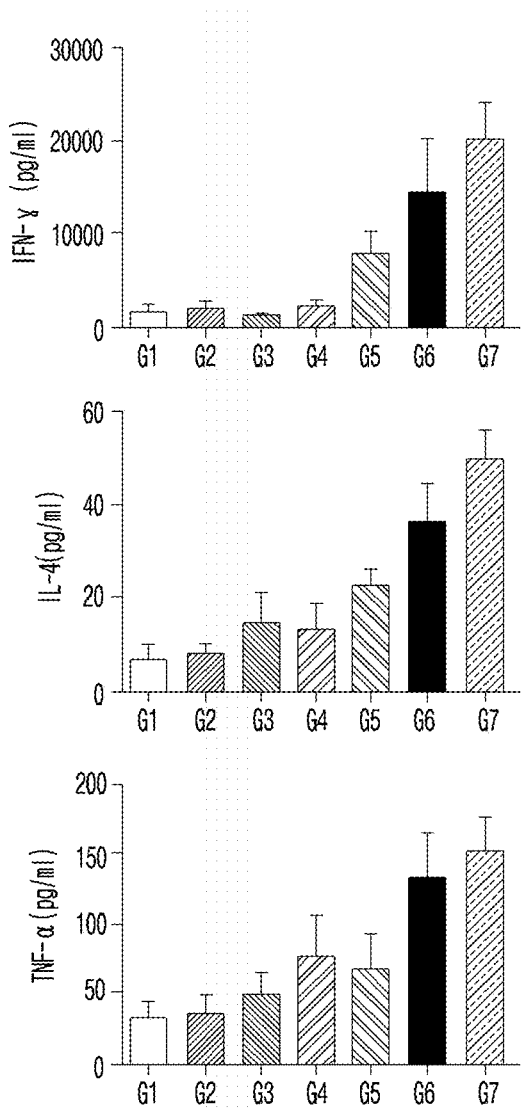
[Fig. 25b]

[Fig. 26]
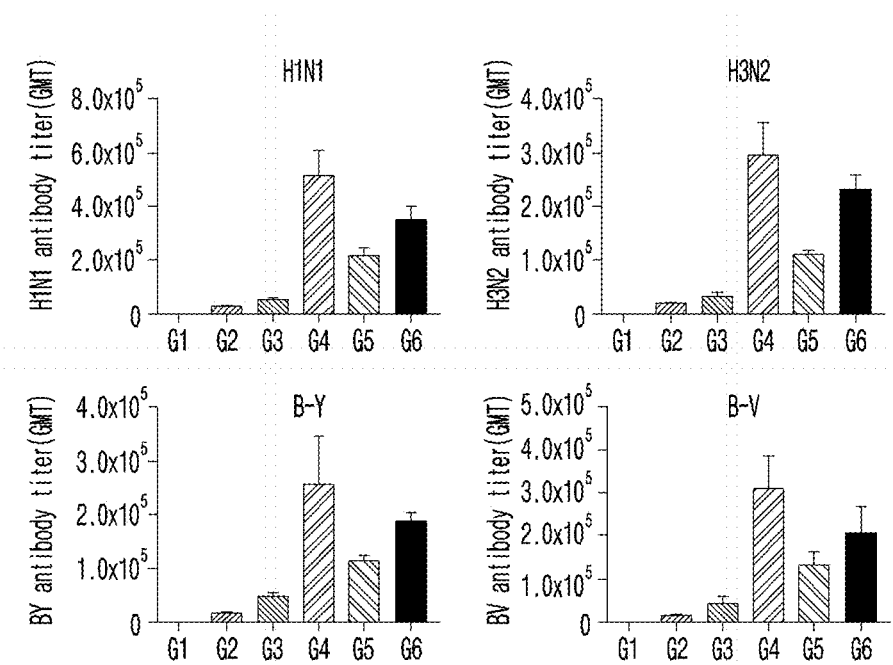

[Fig. 27]
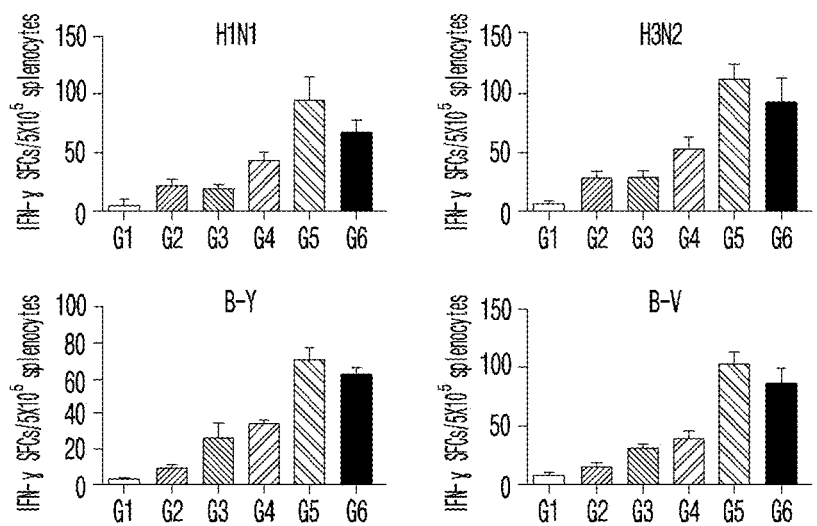

[Fig. 28]
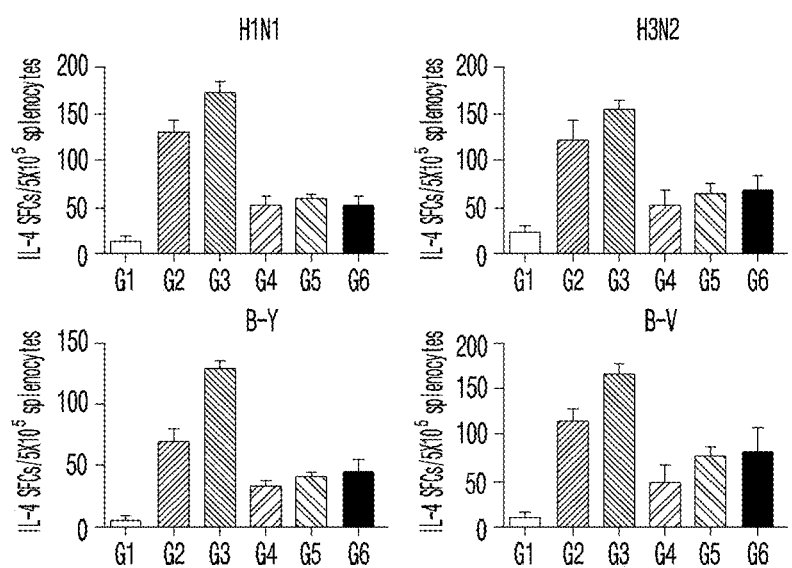

[Fig. 29]
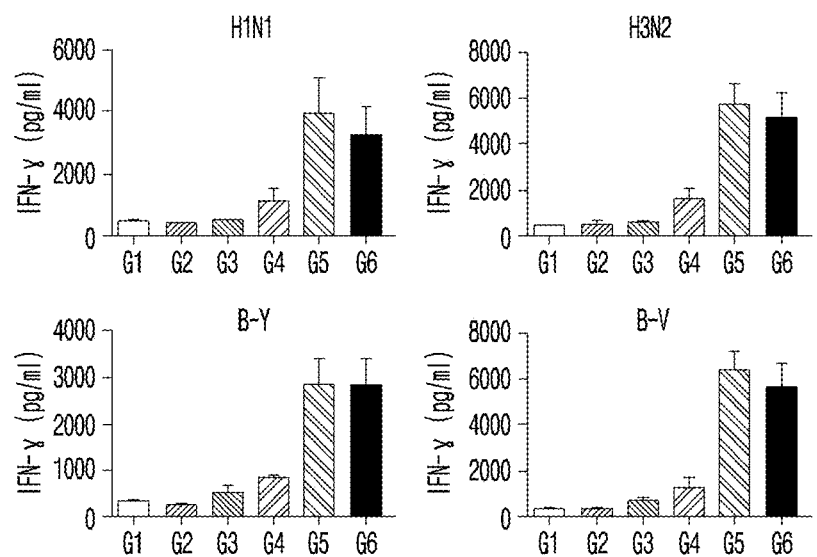

[Fig. 30]
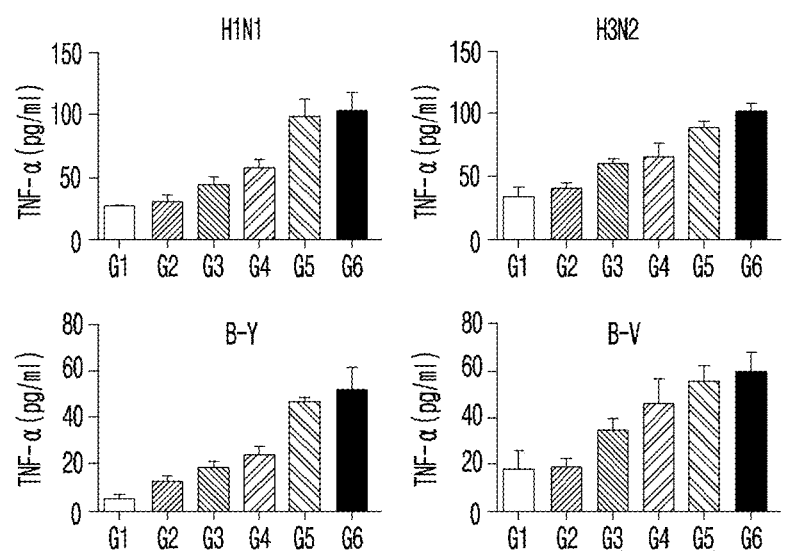

[Fig. 31]
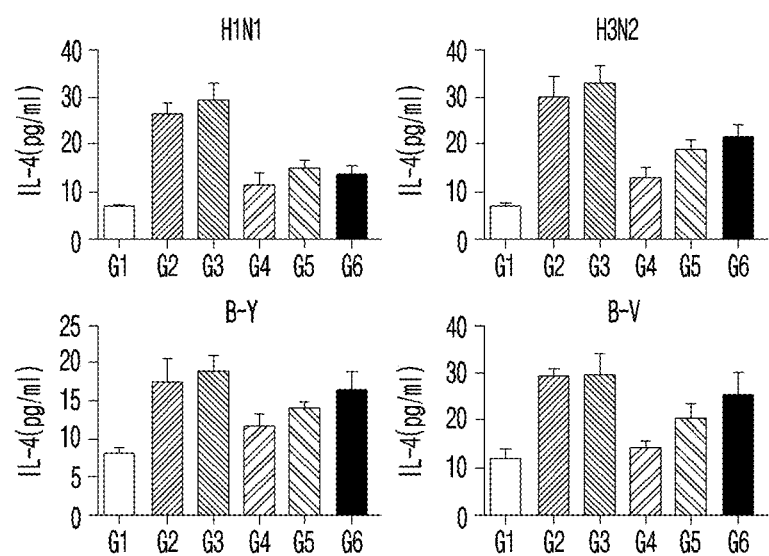

VACCINE ADJUVANT COMPRISING LIPOPEPTIDE-INSERTED LIPOSOME AS EFFECTIVE INGREDIENT AND USE THEREOF

CROSS-REFERENCE TO RELATED APPLICATIONS

This application claims priority to PCT Application No. PCT/KR2018/009173 filed Aug. 10, 2018, entitled "VACCINE ADJUVANT COMPRISING LIPOPEPTIDE-INSERTED LIPOSOME AS EFFECTIVE INGREDIENT AND USE THEREOF," which claims the benefit of and priority to Korean Patent Application No. 10-2018-0005418, filed on Jan. 16, 2018 and Korean Patent Application No. 10-2017-0103788, filed on Aug. 16, 2017, all of which are incorporated herein by reference in their entirety.

BACKGROUND OF THE INVENTION

1. Field of the Invention

The present invention relates to a vaccine adjuvant comprising a lipopeptide-inserted liposome as an active ingredient and a use thereof.

2. Description of the Related Art

Chicken pox or Herpes Zoster is caused by VZV (Varicella-Zoster Virus), and is a disease developed on the skin distributed in the sensory nerves of a single spinal cord or cranial nerve. In the early stage of VZV infection, the virus proliferates in the epidermis and dermis of the skin and then penetrates into surrounding nerve cells and remains latent. Chicken pox develops and rash occurs in the process of proliferation before the latent period, and then, the virus remains dormant in the ganglion. When the body's resistance drops, VZV reactivates and appears in herpes zoster form. The VZV reactivation and the herpes zoster development are associated with decreased cellular immune responses centered on T cells, particularly in aged people and those people receiving immunosuppressive treatment. When herpes zoster develops, bullous lesions appear, and even when the lesions recover, neuralgia remains as an aftereffect. Neuralgia, once developed, is difficult to cure and causes poor quality of life due to severe pain.

If infected with VZV and the initial response is neglected, then it would remain latent, and eventually VZA would be reactivated to cause herpes zoster accompanied by severe pain. In this case, an antiviral agent is generally administered, but it is difficult to induce death or inactivation of VZV, which is likely to have tolerance in the body during the latent period.

Antiviral agents for VZV include acyclovir, germinated cyclofam, famciclovir and the like, of which acyclovir is the most commercialized. However, acyclovir is only effective when administered within 24 hours of chicken pox rash. In other words, acyclovir is not effective as an antiviral agent when administered 24 hours after viral infection or chickenpox rash, or after herpes zoster development caused by reactivation of VZV.

As the number of elderly people and immunosuppressive patients increases, the incidence of herpes zoster increases rapidly in Korea. However, since there is no fundamental treatment, it is necessary to develop a vaccine to prevent it.

Although the commercially available herpes zoster vaccine has been proved for its efficacy in clinical trials, the herpes zoster incidence has been reduced by only 50% by administration of the vaccine, indicating that it has little efficacy. In addition, since the commercially available herpes zoster vaccine is an attenuated live vaccine, the vaccine has limitations in administration to immunosuppressive patients, pregnant women, and those who are likely to become pregnant, with a high incidence of herpes zoster. Because herpes zoster virus remains latent in the ganglion and herpes zoster is developed by reactivation of VZV when body resistance drops, it is more important to induce cell-mediated immune response than humoral immune response. Therefore, it is necessary to develop a herpes zoster vaccine that is effective and safe and can induce cell-mediated immune response.

The molecular pattern of an antigen affects the results of the immune response. This is particularly important when the entire pathogenic microorganism is used as an antigen, which is a mixture of several types of pathogen associated molecular pattern (PAMP) ligands such as lipopolysaccharides, nucleic acids, lipoproteins or proteins. Pathogen recognition receptors (PRRs) on the surface of antigen presenting cells are involved in the type of immune response induced by recognizing PAMPs and promoting the signals for inducing various costimulatory molecules and cytokines. For example, interferon gamma and IL-12 induce Th1 cell responses, which are important for immune response to virus infection. Th1 type immune responses induce more IgG2a or IgG2b production and potent cell-mediated immune responses.

In this regard, Korean Patent No. 10-1723605 describes a DNA vaccine composition for preventing and treating herpes zoster comprising a plasmid containing an insertion site of a VZV-derived gene encoding a protein of VZV, and Korean Patent Publication No. 10-2014-0022799 describes a chicken pox and herpes zoster vaccine compositions comprising the protein encoded by genomic DNA of VZV MVA06 isolated from a Korean patient and its open reading frame.

Thus, the present inventors have studied to develop a herpes zoster vaccine that is safe and induces not only humoral immune response but also cell-mediated immune response. In the course of the study, the present inventors prepared Lipo-pam, a liposome-type composite adjuvant containing Pam3-CSKKKK (SEQ. ID. NO: 2) (Pam3CSK4) lipopeptide and lipids, and confirmed that the vaccine composition containing Poly(I:C) and an antigen in the prepared adjuvant highly induced humoral immune response as well as cell-mediated immune response to a small molecular weight recombinant protein antigen. The present inventors also confirmed that the vaccine composition of the present invention prepared using a variety of lipopeptides, including Pam3-CSKKKK (SEQ. ID. NO: 2), Dhc-SKKKK (SEQ. ID. NO: 3), PamDhc-SKKKK (SEQ. ID. NO: 3), etc., or gE (glycoprotein E) antigen of varicella-zoster virus as well as gE (glycoprotein E) antigen of Japanese encephalitis virus or seasonal inactivated influenza virus antigen showed significant effects. Accordingly, the present invention has been completed by confirming that the vaccine composition comprising the adjuvant of the present invention can be effectively used commercially without limitations in the type of lipopeptides and antigens.

PRIOR ART REFERENCE

Patent Reference (Patent Reference 1) Korean Patent No. 10-1723605
(Patent reference 2) Korean Patent Publication No. 10-2014-0022799

SUMMARY OF THE INVENTION

It is an object of the present invention to provide a vaccine adjuvant comprising a lipopeptide-inserted liposome as an active ingredient, a vaccine composition comprising the same, and a use thereof.

To achieve the above object, the present invention provides a vaccine adjuvant comprising a lipopeptide-inserted liposome as an active ingredient.

The present invention also provides a vaccine composition comprising the adjuvant and antigen of the present invention.

The present invention also provides a preventive or therapeutic agent for viral infection comprising the vaccine composition of the present invention as an active ingredient.

In addition, the present invention provides a preventive or therapeutic agent for cancer comprising the vaccine composition of the present invention as an active ingredient.

In addition, the present invention provides a preventive or therapeutic method for viral infection comprising a step of administrating the vaccine composition of the present invention to subject.

In addition, the present invention provides a preventive or therapeutic method for cancer comprising a step of administrating the vaccine composition of the present invention to subject.

In addition, the present invention provides use of the vaccine composition of the present invention for using to prepare a preventive or therapeutic agent for viral infection.

In addition, the present invention provides use of the vaccine composition of the present invention for using to prepare a preventive or therapeutic agent for cancer.

Advantageous Effect

The vaccine composition comprising Lipo-Pam, a composite adjuvant containing lipids and lipopeptides of the present invention, highly induced cell-mediated immune response as well as humoral immune response, and the vaccine composition prepared by using gE antigen of varicella-zoster virus as well as gE antigen of Japanese encephalitis virus or seasonal inactivated influenza virus antigen showed significant effects. Therefore, the composition of the present invention can be effectively used commercially.

BRIEF DESCRIPTION OF THE DRAWINGS

FIG. 1 is a schematic diagram illustrating the production of pPGXII-VZV gE plasmid in which gE gene of VZV was introduced into pPGXII vector.

FIG. 2 is a set of diagrams illustrating the results of SDS-PAGE performed according to the purification steps of the recombinant VZV gE antigen (A) and the final, purified recombinant VZV gE antigen (B). M is a marker for checking the size, 1 is a cell culture medium, 2 is a butyl-sepharose chromatography eluent, 3 is a DEAE-sepharose chromatography eluent, 4 is a CHT chromatography eluent, 5 is a SP-sepharose chromatography eluent, and 6 means after concentrating-desalting filtration.

FIG. 3 is a set of graphs comparing the VZV gE antibody titers (A) and the antibody isotypes (B) according to the preparation method of the liposome and the proportion of the components contained in the liposome.

FIG. 4 is a set of graphs comparing the results of ELISPOT assay of IFN-γ and IL-4 (A) and the results of ELISA assay of IFN-γ, IL-4 and TNF-α (B) for VZV recombinant gE antigen of the recombinant vaccine according to the preparation method of the liposome and the proportion of the components contained in the liposome.

FIG. 5 is a diagram confirming the structure of the vaccine prepared using Lipo-pam observed with a confocal microscope.

FIG. 6 is a graph comparing the total IgG antibody titers for the vaccine composition comprising the VZV recombinant gE antigens and the adjuvants prepared by varying the composition of lipids and Pam3-CSKKKK (SEQ. ID. NO: 2) and the dose of Poly(I:C) contained in Lipo-pam.

FIG. 7 is a set of graphs comparing the results of ELISPOT assay of IFN-γ and IL-4 (A) and the results of ELISA assay of IFN-γ, IL-4 and TNF-α (B) for the vaccine composition comprising the VZV recombinant gE antigens and the adjuvants prepared by varying the composition of lipids and Pam3-CSKKKK (SEQ. ID. NO: 2) and the dose of Poly(I:C) contained in Lipo-pam.

FIG. 8 is a graph comparing the total IgG antibody titers for the vaccine compositions comprising the adjuvants prepared by varying the dose of lipids included in Lipo-pam and the different doses of the recombinant VZV gE antigen.

FIG. 9 is a set of graphs comparing the results of ELISPOT assay of IFN-γ and IL-4 (A) and the results of ELISA assay of IFN-γ, IL-4 and TNF-α (B) for the vaccine composition comprising the adjuvants prepared by varying the dose of lipids included in Lipo-pam and the different doses of the recombinant VZV gE antigen.

FIG. 10 is a graph comparing the total IgG antibody titers for the vaccine compositions comprising the adjuvants prepared by varying the doses of lipids and Poly(I:C) contained in Lipo-pam and the different doses of the recombinant VZV gE antigen.

FIG. 11 is a set of graphs comparing the results of ELISPOT assay of IFN-γ and IL-4 (A) and the results of ELISA assay of IFN-γ, IL-4 and TNF-α (B) for the vaccine composition comprising the adjuvants prepared by varying the doses of lipids and Poly(I:C) contained in Lipo-pam and the different doses of the recombinant VZV gE antigen.

FIG. 12 is a graph comparing the total IgG antibody titers against the recombinant VZV gE antigen of the attenuated herpes zoster vaccine and the recombinant vaccine according to the adjuvant formulation.

FIG. 13 is a set of graphs comparing the results of ELISPOT assay of IFN-γ and IL-4 (A) and the results of ELISA assay of IFN-γ, IL-4 and TNF-α (B) for the VZV recombinant gE antigen of the attenuated herpes zoster vaccine and the recombinant vaccine according to the adjuvant formulation.

FIG. 14 is a graph comparing the frequency of CD4+ T cells secreting cytokines for the attenuated herpes zoster vaccine and the recombinant vaccine according to the adjuvant formulation.

FIG. 15 is a set of graphs comparing the multifunctionality of CD4+ T cells for the attenuated herpes zoster vaccine and the recombinant vaccine according to the adjuvant formulation.

FIG. 16 is a graph comparing the total IgG antibody titers against the recombinant VZV gE antigens of the attenuated herpes zoster vaccine and the recombinant vaccine according to the adjuvant composition and formulation.

FIG. 17 is a set of graphs comparing the results of ELISPOT assay of IFN-γ and IL-4 (A) and the results of ELISA assay of IFN-γ, IL-4 and TNF-α (B) for the recombinant VZV gE antigens of the attenuated herpes zoster vaccine and the recombinant vaccine according to the adjuvant composition and formulation.

FIG. 18 is a graph comparing the total IgG antibody titers against the recombinant VZV gE antigen of the recombinant vaccine according to the composition and preparation method of Lipo-pam.

FIG. 19 is a set of graphs comparing the results of ELISPOT assay of IFN-γ and IL-4 (A) and the results of ELISA assay of IFN-γ, IL-4 and TNF-α (B) for the recombinant VZV gE antigen of the recombinant vaccine according to the composition and preparation method of Lipo-pam.

FIG. 20 is a graph comparing the total IgG antibody titers against the recombinant VZV gE antigen of the recombinant vaccine according to the types and doses of lipids, types of immunoactive substances, and doses of the recombinant VZV gE antigen.

FIG. 21 is a set of graphs comparing the results of ELISPOT assay of IFN-γ and IL-4 (A) and the results of ELISA assay of IFN-γ, IL-4 and TNF-α (B) for the recombinant VZV gE antigen of the recombinant vaccine according to the types and doses of lipids, types of immunoactive substances, and doses of the recombinant VZV gE antigen.

FIG. 22 is a graph comparing the total IgG antibody titers against the recombinant VZV gE antigen of the recombinant vaccine according to the types of lipopeptide constituting Lipo-pam.

FIG. 23 is a set of graphs comparing the results of ELISPOT assay of IFN-γ and IL-4 (A) and the results of ELISA assay of IFN-γ, IL-4 and TNF-α (B) for the recombinant VZV gE antigen of the recombinant vaccine according to the types of lipopeptide constituting Lipo-pam.

FIG. 24 is a set of graphs comparing the total IgG antibody titer against the recombinant JEV gE antigen (A) and the total IgG antibody titer against the inactivated JEV antigen (B).

FIG. 25 is a set of graphs comparing the results of ELISPOT assay of IFN-γ and IL-4 (A) and the results of ELISA assay of IFN-γ, IL-4 and TNF-α (B) for the Japanese encephalitis virus gE antigen of the recombinant vaccine according to the adjuvant formulation.

FIG. 26 is a set of graphs comparing the total IgG antibody titers against four strains of seasonal inactivated influenza virus (H1N1, H3N2, B-Y or B-V) according to the adjuvant formulation.

FIG. 27 is a set of graphs illustrating the results of ELISPOT assay of IFN-γ of four strains of seasonal inactivated influenza virus (H1N1, H3N2, B-Y or B-V) according to the adjuvant formulation.

FIG. 28 is a set of graphs illustrating the results of ELISPOT assay of IL-4 of four strains of seasonal inactivated influenza virus (H1N1, H3N2, B-Y or B-V) according to the adjuvant formulation.

FIG. 29 is a set of graphs illustrating the results of ELISA assay of IFN-γ of four strains of seasonal inactivated influenza virus (H1N1, H3N2, B-Y or B-V).

FIG. 30 is a set of graphs illustrating the results of ELISA assay of TNF-α of four strains of seasonal inactivated influenza virus (H1N1, H3N2, B-Y or B-V).

FIG. 31 is a set of graphs illustrating the results of ELISA assay of IL-4 of four strains of seasonal inactivated influenza virus (H1N1, H3N2, B-Y or B-V).

DESCRIPTION OF THE PREFERRED EMBODIMENTS

Hereinafter, the present invention is described in detail.

The present invention provides a vaccine adjuvant comprising a lipopeptide-inserted liposome as an active ingredient.

The lipopeptide can be composed of several amino acids and fatty acids bound to glycerol molecules. The number of amino acid constituting lipopeptide or fatty acid in the glycerol molecule can be one or more. At this time, the fatty acid and the amino acid can be chemically modified. The lipopeptide can be a part of a molecule derived from gram positive or gram negative bacteria or mycoplasma or a lipoprotein in the form of a whole molecule. For example, the lipopeptide can be any one or more selected from the group consisting of Pam3-CSKKKK (SEQ. ID. NO: 2), PHC-SKKKK (SEQ. ID. NO: 3), Pam2Cys-SKKKK (SEQ. ID. NO: 3), PamDhc-SKKKK (SEQ. ID. NO: 3), Pam-CSKKKK (SEQ. ID. NO: 2), Dhc-SKKKK (SEQ. ID. NO: 3) and FSL-1 (i.e., Pam2CGDPKHPKSF; SEQ. ID. NO: 4). The lipopeptide can be included in the liposome at the concentration of 20 to 250, 20 to 50, 50 to 250, 150 to 250, 50 to 150, 20 to 2500, 20 to 500, 50 to 2500, 150 to 2500 or 50 to 1500 μg/dose.

The liposome can be composed of lipids. The lipid can be cationic, anionic or neutral lipid. For example, the lipid can be any one or more selected from the group consisting of DOTAP (1,2-Dioleoyl-3-Trimethylammonium-Propane), DOPE (1,2-dioleoyl-sn-glycero-3-phosphoethanolamine), DDA (Dimethyldioctadecylammonium), DC-chol (3β-[N—(N′,N′-Dimethylaminoethane)-carbamoyl]cholesterol), DOPG (1,2-Dioleoyl-sn-Glycero-3-[Phospho-rac-(1-glycerol)]), DPPC (1,2-dipalmitoyl-sn-glycero-3-phosphocholine), DOPC (1,2-dioleoyl-sn-glycero-3-phosphocholine) and cholesterol. The lipid can be included in the liposome at the concentration of 15 to 300, 15 to 150, 15 to 90, 15 to 50, 15 to 40, 20 to 30, 15 to 3000, 15 to 1500, 15 to 900, 15 to 500, 15 to 400 or 20 to 300 μg/dose.

The vaccine adjuvant according to the present invention can further include an immunoactive substance. The immunoactive substance can be any one or more selected from the group consisting of Poly(I:C), QS21, MPLA (Monophosphoryl Lipid A), CpG and Flagellin. The Poly(I:C) has been used as a potent inducer of type 1 interferon in in vitro and in vivo studies. Moreover, the Poly(I:C) has been known to stably and maturely form dendritic cells, the most potent antigen-presenting cells in mammals (Rous, R. et al 2004, International Immunol, 16:767-773). According to the previous reports, Poly(I:C) is a potent IL-12 inducer. The said IL-12 is an important immunoactive substance inducing cell-mediated immune response and IgG2a or IgG2b antibody formation by promoting Th1 development. The length of the Poly(I:C) can be 50 to 5,000 bp. The Poly(I:C) can be included in the adjuvant at the concentration of 10 to 150, 10 to 90, 10 to 50, 10 to 30, 30 to 60, 30 to 90, 30 to 150, 30 to 50, 10 to 1500, 10 to 900, 10 to 500, 10 to 300, 30 to 600, 30 to 900, 30 to 1500, or 30 to 500 μg/dose.

The QS21 is a fraction of a saponin substance called triterpene glucoside having a molecular weight of 1990.14 Da extracted from the bark of *Quillaja saponaria Molina* in South America. When combined with lipids such as MPLA and cholesterol, the QS21 is known to induce humoral and cell-mediated immune responses by secreting Th1-type cytokines from antigen-presenting cells such as macrophages and dendritic cells. The QS21 can be included in the adjuvant at the concentration of 1 to 150, 1 to 90, 1 to 50, 1 to 30, 3 to 60, 3 to 90, 3 to 150, 3 to 50, 1 to 1500, 1 to 900, 1 to 500, 1 to 300, 3 to 600, 3 to 900, 3 to 1500 or 3 to 500 μg/dose.

The present invention also provides a vaccine composition comprising the adjuvant and antigen of the present invention.

The adjuvant can have the characteristics as described above. For example, the adjuvant can include a lipopeptide-inserted liposome, and can further include an immunoactive substance.

The antigen include all substances that can be recognized by the host's immune system and trigger an immune response when they enter the host's body, which can be proteins, recombinant proteins, glycoproteins, peptides, polysaccharides, lipopolysaccharides or polynucleotides of the pathogen. For example, the antigen can be exemplified by gE (glycoprotein E) of varicella-zoster virus; gE (glycoprotein E) antigen of Japanese encephalitis virus; seasonal inactivated influenza virus antigen; haemagglutinin antigen and neuraminidase antigen of influenza virus; pertussis toxin antigen of *Bordetella pertussis*, filamentous haemagglutinin antigen and pertactin antigen; human papilloma virus (HPV) antigen, capsule polysaccharide antigen of *Helicobacter pylori* A, B, C, Y and W-135 group; tetanus toxoid antigen of *Clostridium tetani*; diphtheria toxoid antigen of diphtheria; *Streptococcus* pnemoniae type 3 capsular polysaccharide antigen; tuberculosis antigen; GP-120 and GP-160 antigens of human immunodeficiency virus (HIV); cholera toxin B subunit antigen; staphylococcal enterotoxin B antigen; *Shigella* polysaccharides antigen; vesicular stomatitis virus glycoprotein antigen; cytomegalovirus (CMV) antigen, hepatitis A (HAV), B (HBV), C (HCV), D (HDV) and G (HGV) antigens; respiratory synctytial virus (RSV) antigen or herpes simplex antigen.

The vaccine composition can additionally include buffers, isotonic agents, preservatives, stabilizers and solubilizers. As the buffer, phosphate, acetate, ammonium phosphate, ammonium carbonate, citrate and the like can be used.

The vaccine can induce not only antigen-specific humoral immune response but also cell-mediated immune response highly.

The vaccine can enhance Th1 immune response. IgG2a or IgG2b antibody that enhances Th1 immune response effective for antiviral and anticancer immune responses is produced by the cytokines generated by helper T cell 1 (Th1). Therefore, the vaccine composition of the present invention can be used as a preventive or therapeutic agent for viral infection or cancer.

In a specific embodiment of the present invention, the present inventors first prepared a recombinant varicella-zoster virus gE antigen (see FIGS. 1 and 2), and prepared Lipo-Pam by mixing DC-Chol, DOPE or DPPC lipid with Pam3-CSKKKK (SEQ. ID. NO: 2), to which Poly(I:C) or QS21 was added as an immunoactive substance. Then, a recombinant vaccine against varicella-zoster virus was prepared by adding the prepared recombinant varicella-zoster virus gE antigen thereto.

In the recombinant vaccine, Pam3-CSKKKK (SEQ. ID. NO: 2) formed liposome with lipids, and the recombinant VZV gE antigen was attached on the surface of liposome (FIG. 5).

The recombinant vaccine induced not only humoral immune response but also cell-mediated immune response highly (see FIGS. 3, 4, and 6 to 21).

Lipo-pam was prepared by mixing various types of lipopeptide with DC-Chol and DPPC, and a recombinant vaccine was prepared by adding Poly(I:C) and recombinant VZV gE antigen to the Lipo-pam. The prepared recombinant vaccine induced not only humoral immune response but also cell-mediated immune response highly (see FIGS. 22 and 23).

A recombinant vaccine against Japanese encephalitis virus was also prepared by adding Poly(I:C) and recombinant Japanese encephalitis virus gE antigen to the Lipo-Pam prepared by mixing DC-Chol, DPPC and Pam3-CSKKKK (SEQ. ID. NO: 2). The prepared recombinant vaccine induced not only humoral immune response but also cell-mediated immune response highly (see FIGS. 24 and 25).

In addition, A recombinant vaccine against seasonal inactivated influenza virus was prepared by adding Poly(I:C) and 4 strains of seasonal inactivated influenza virus antigens to the Lipo-Pam prepared by mixing DC-Chol, DOPE or DPPC and Pam3-CSKKKK (SEQ. ID. NO: 2). The prepared recombinant vaccine induced not only humoral immune response but also cell-mediated immune response highly (see FIGS. 26 and 31).

Therefore, the vaccine composition of the present invention comprising the lipopeptide-inserted Lipo-Pam as an adjuvant can be effectively used commercially since it has an immune-enhancing effect without limitation on the type of antigen.

The present invention also provides a preventive or therapeutic agent for viral infection or cancer comprising the vaccine composition of the present invention as an active ingredient.

The vaccine composition can have the characteristics as described above. For example, the vaccine composition can comprise an adjuvant and an antigen. The adjuvant can include a lipopeptide-inserted liposome, and can further include an immunoactive substance.

The preventive or therapeutic agent of the present invention can include a pharmaceutically acceptable carrier and can be formulated for human or animals. It can be administered by various routes. The route of administration includes oral, intraperitoneal, intravenous, intramuscular, subcutaneous and intradermal administration. Preferably, the formulation is administered as an injection. The injection can be prepared by using aqueous solvents such as physiological saline and Ringer's solution, and non-aqueous solvents such as vegetable oils, higher fatty acid esters (e.g., ethyl oleate, etc.) and alcohols (e.g., ethanol, benzyl alcohol, propylene glycol, glycerin, etc.). It can include pharmaceutical carriers such as stabilizers to prevent deterioration (e.g., ascorbic acid, sodium bisulfite, sodium pyrosulfite, BHA, tocopherol, EDTA, etc.), emulsifiers, buffers for pH control, preservatives to prevent microbial growth (e.g., phenyl mercury nitrate, thimerosal, benzalkonium chloride, phenol, cresol, benzyl alcohol, etc.).

The preventive or therapeutic agent of the present invention can be administered by the pharmaceutically effective amount. The term "pharmaceutically effective amount" means the amount that can exhibit a vaccine effect and at the same time not cause side effects or serious or excessive immune response, and the exact dose will vary depending on the antigen to be included in the vaccine. The effective dose of the preventive or therapeutic agent of the present invention can be easily determined according to age, weight, health condition, gender and drug sensitivity, administration route and administration method by those in the art. The administration frequency is once a day or a few times a day.

Hereinafter, the present invention will be described in detail by the following examples.

However, the following examples are only for illustrating the present invention, and the contents of the present invention are not limited thereto.

Example 1. Preparation of Recombinant Varicella-Zoster Virus gE Antigen

<1-1> Construction of Plasmid

First, a gene (SEQ. ID. NO: 1) was synthesized to include restriction enzyme recognition sequences (Nhe I site at 5' and Xho I site at 3') and kozak sequence in the outer region of the gE (glycoprotein E) gene expression region of VZV. At this time, a codon-optimized sequence for CHO cells, in the form of removing the C-terminal anchor domain from ORF68 (glycoprotein E) of entire human herpesvirus type 3 (HHV-3) genome, was used as a template. The 1.6 kb gE gene of VZV represented by SEQ. ID. NO: 1 was digested with Nhe I and Xho I restriction enzymes, and subcloned into pPGXII vector. As a result, pPGXII-VZV gE, the VZV gE expression plasmid, was prepared (FIG. 1).

<1-2> Selection of Cell Line

DNA of the pPGXII-VZV gE plasmid prepared in Example <1-1> was liberalized with Ahd I restriction enzyme, which was transfected in CHO DG44(S)-EX cells passaged 6 times in a medium containing HT (Hypoxantine-Thymidine) together with pDCH1P(dhfr) plasmid DNA by electroporation. Then, the transformed cells were inoculated in a medium containing HT. When the cells were sufficiently grown, the cells were cultured in a selection medium without HT. About 2 weeks later, the initially adapted cell groups were obtained. Using the obtained cell groups, dot blot and Western blot were performed to select four highly productive strains from the initially adapted cell groups. The selected strains were diluted by limiting dilution method and each strain was inoculated in 10 plates of 96-well plates to be 1 cell/well to isolate single cell line. Colonies of the isolated single cell lines were transferred to 24-well plates, cultured, and then suspension-cultured in Erlenmeyer flasks when sufficient cell numbers were secured. After passage six times, when the cells were proliferating at a constant rate while maintaining viability of 95% or more, fed-batch culture was performed to confirm the productivity and stability. The final cell line was selected in consideration of cell growth and productivity among the five candidate cell lines having high productivity and maintaining stability of 80% or more.

<1-3> Culture of Cell Line

The cell line finally selected in Example <1-2> was inoculated in a 7.5 l jar fermentor containing HyCell CHO (GE Healthcare) medium after adding EfficientFeed C+ (Invitrogen) at the density of $6.5 \times 10^6$ cells/a, and cultured. At this time, the fermentor was operated at 32° C., DO 30%, 100 rpm, and pH of the medium was maintained above 6.8. The contents of glucose and lactic acid in the fermentor were analyzed every day, and when the glucose content dropped below 20 mmol/l, 45% D-glucose was added at the concentration of 1 v/v % and cultured for 10 days.

<1-4> Antigen Purification

The culture medium was recovered from the cells cultured in Example <1-3> using a depth-filter, and the recombinant gE antigen of VZV was purified therefrom. Particularly, the recombinant VZV gE antigen was purified by 4-step column chromatography using butyl-sepharose, DEAE-sepharose, CHT hydroxyapatite and SP-sepharose sequentially, and one-time UF/DF for buffer exchange.

As a result, as shown in FIG. 2, the purified recombinant VZV gE antigen showed a molecular weight of about 70 kDa (FIG. 2).

Example 2. Comparison of Immunogenicity of Recombinant Vaccine According to Doses of Lipopeptide and Poly(I:C)

<2-1> Preparation and Administration of Test Vaccine

First, to prepare DC-Chol:DOPE liposome, DC-Chol and DOPE were dissolved in chloroform, respectively, and then the organic solvent was vaporized with nitrogen gas while rotating the glass vessel so that the mixed solution was evenly distributed on the base wall of the vessel. At this time, a thin film was formed on the base wall. The organic solvent remaining in the formed film was removed by storing in a vacuum desiccator for 1 hour. Distilled water was added to the completely dried lipid film, followed by sufficient rehydration for 10 minutes using an ultrasonic bath. When multilamella vesicle (MLV) suspension was produced, 2× buffer solution (pH 7.0) containing 300 mM NaCl in 20 mM sodium phosphate was added in the same amount as distilled water. The resulting MLV was subjected to 5 cycles of sonication (5 minutes/cycle) under the conditions of 3 seconds/3 seconds (pulse on/off) to prepare DC-Chol:DOPE liposome in the form of small unilamellar vesicle (SUV).

In addition, Lipo-Pam was prepared in the same manner as the DC-Chol:DOPE liposome except that DC-Chol, DOPE and Pam3-CSKKKK (SEQ. ID. NO: 2) were dissolved in an organic solvent, respectively, DC-Chol and DOPE were mixed at the ratio of 3:7, and Pam3-CSKKKK (SEQ. ID. NO: 2) was added thereto at the concentration of 25 μg/dose or 100 μg/dose.

At this time, L-pampo, the control, was prepared by mixing 25 μg of Pam3-CSKKKK (SEQ. ID. NO: 2), which is lipopeptide, with 20 μg or 200 μg of Poly(I:C).

Thereafter, the adjuvant was mixed with the composition as shown in Table 1 below, and VZV gE antigen was added to the mixture at the concentration of 5 μg/dose to prepare test vaccines. In the cases of G2, G5 and G9 groups, the mixture was sonicated and the antigen was added to prepare test vaccines. The prepared vaccines were injected intramuscularly to 6 week old C57BL/6 female mice (Orient Bio Inc., Korea) twice at two-week intervals.

TABLE 1

| Test Group | Preparation conditions of test vaccines for each test group<br>Composition |
|---|---|
| G1 | PBS |
| G2 | liposome(DC-Chol:DOPE(3:7) 125 μg) + L-Pampo(Pam3-CSKKKK (SEQ. ID. NO: 2) 25 μg + Poly(I:C) 20 μg) + antigen 5 μg/sonication |
| G3 | liposome(DC-Chol:DOPE(3:7) 125 μg) + L-Pampo(Pam3-CSKKKK (SEQ. ID. NO: 2) 25 μg + Poly(I:C) 200 μg) + antigen 5 μg |
| G4 | liposome(DC-Chol:DOPE(3:7) 125 μg) + Poly(I:C) 20 μg + antigen 5 μg |
| G5 | Lipo-Pam(DC-Chol:DOPE(3:7) 125 μg + Pam3-CSKKKK (SEQ. ID. NO: 2) 25 μg) + antigen 5 μg/sonication |
| G6 | Lipo-Pam(DC-Chol:DOPE(3:7) 125 μg + Pam3-CSKKKK (SEQ. ID. NO: 2) 25 μg) + Poly(I:C) 20 μg + antigen 5 μg |
| G7 | Lipo-Pam(DC-Chol:DOPE(3:7) 125 μg + Pam3-CSKKKK (SEQ. ID. NO: 2) 25 μg) + Poly(I:C) 200 μg + antigen 5 μg |
| G8 | Lipo-Pam(DC-Chol:DOPE(3:7) 125 μg + Pam3-CSKKKK (SEQ. ID. NO: 2) 100 μg) + Poly(I:C) 200 μg + antigen 5 μg |
| G9 | Lipo-Pam(DC-Chol:DOPE(3:7) 125 μg + Pam3-CSKKKK (SEQ. ID. NO: 2) 25 μg) + Poly(I:C) 200 μg/sonication + antigen 5 μg |

<2-2> Analysis of Humoral Immune Response

In order to analyze the humoral immune response induced by the test vaccine administered in Example <2-1>, the antibody titer was determined by analyzing the antigen-specific antibody formation with ELISA by separating the serum of mice at week 0 before immunization, week 2, 2 weeks after the first vaccination and week 4, 2 weeks after the second vaccination.

First, the total IgG antibody titer against the recombinant VZV gE antigen was confirmed by the following method. Particularly, the purified recombinant VZV gE antigen was coated on a 96-well microplate at the concentration of 100 ng/well, and then reacted for 1 hour by adding 1% bovine serum albumin to prevent nonspecific binding. The microplate was washed. The serially diluted serum was added to each well of the plate, followed by reaction at 37° C. for 2 hours. Anti-mouse IgG-HRP (horse radish peroxidase, KPL, USA) was added to the plate for 1 hour as a secondary antibody, followed by reaction under the same conditions. The reacted microplate was washed and the color reagent TMB (3,3',5,5'-tetramethyl benzidine) peroxidase substrate (KPL, USA) was added thereto, followed by reaction at room temperature for 10 minutes. The color reaction was terminated using a stop solution, and then OD was measured at 450 nm using an ELISA reader. Antibody titer was defined as a reciprocal number of the antibody dilution fold showing an OD value corresponding to twice the negative control OD value.

On the other hand, the antibody isotype titer against the recombinant VZV gE antigen was analyzed by the same method as the total antibody titer against the recombinant VZV gE antigen except that goat anti-mouse IgG1, goat anti-mouse IgG2a, goat anti-mouse IgG2b or goat anti-mouse IgG2c was used as the primary antibody and rabbit anti-goat IgG-HRP was used as the secondary antibody.

As a result, as shown in FIG. 3A, the total IgG antibody titer against the recombinant VZV gE antigen was highest in the G3 group administered with the vaccine prepared by mixing DC-Chol:DOPE liposome and L-pampo (Poly(I:C) 200 μg+Pam3-CSKKKK (SEQ. ID. NO: 2) 25 μg). When comparing the humoral immune response according to whether Lipo-pam and Poly(I:C) were mixed, the total IgG was higher in the G6 group administered with the vaccine prepared by mixing Lipo-pam and Poly(I:C) compared to the G5 group administered with the vaccine prepared by mixing antigens with Lipo-pam alone (FIG. 3A).

As shown in FIG. 3B, analysis of antibody isotype against the recombinant VZV gE antigen showed higher IgG2b and IgG2c type antibody titers compared to IgG1 in all test groups. In particular, IgG2 type antibody titer was high in the G3 group in which L-pampo was mixed with liposome and the G6 group in which Poly(I:C) was mixed with Lipo-pam (FIG. 3B).

<2-3> Analysis of Cell-Mediated Immune Response

The cell-mediated immune response induced by the test vaccine administered in Example <2-1> was analyzed by ELISPOT and cytokine ELISA performed after isolating whole splenocytes by extracting the spleens from the mice at week 4, 2 weeks after the 2$^{nd}$ vaccination.

Particularly, in order to perform ELISPOT assay, the ELISPOT plate attached with anti-IFN-γ or anti-IL-4 was washed with PBS, and then the plate was activated by adding complete media. After distributing the mouse splenocytes in the ELISPOT plate at the density of 5×10$^5$ cells/well, the recombinant VZV gE antigen prepared in Example 1 was added thereto, followed by reaction in a 37° C., 5% CO$_2$ incubator for 24 hours or 48 hours. Then, the splenocytes were removed and the plate was washed with PBS. The biotinylated antibodies in Mouse IFN-γ ELISpot$^{PLUS}$ kit (Mabtech, Sweden) and Mouse IL-4 ELISpot$^{PLUS}$ kit (Mabtech, Sweden) were diluted in PBS containing 0.5% FBS and added to each well of the plates, respectively, followed by reaction at room temperature for 2 hours. After washing the plate, the HRP-conjugated streptavidin was added to each well of the plate, followed by reaction at room temperature for 1 hour. The plate was washed, to which the color reagent TMB was added, followed by reaction until distinct spots appeared. Upon completion of the reaction, tertiary distilled water was added to terminate the reaction. The plate was washed with distilled water several times, dried at room temperature and the spots were calculated using an ELISPOT reader.

Meanwhile, in order to perform cytokine ELISA, the mouse splenocytes were distributed in a 96-well plate at the density of 1.5×10$^6$ cells/well, to which the recombinant VZV gE antigen prepared in Example 1 was added, followed by reaction in a 37° C., 5% CO$_2$ incubator for 48 hours. The culture solution was transferred to tubes for each test group, and the supernatant obtained by centrifugation at 4° C. at 3000 rpm for 5 minutes was used as a sample for performing cytokine ELISA. The antibodies for coating included in Mouse IFN-γ ELISA kit (BD, USA), Mouse IL-4 ELISA kit (BD, USA) and Mouse TNF-α ELISA kit (BD, USA) were diluted in a coating buffer and distributed in a 96-well plate, and the plate was coated at 37° C. for 2 hours. The plate was washed with PBST, to which 10% FBS was added, followed by blocking at 37° C. for 1 hour. After washing the plate, the standard solution and the splenocyte culture solution obtained above were distributed in the plate (100 μl/well), followed by reaction at room temperature for 2 hours. The plate was washed, to which a working detector prepared by mixing the biotinylated antibody and the HRP-conjugated streptavidin was added at the concentration of 100 μl/well, followed by reaction at room temperature for 1 hour. After washing the plate, the color reagent TMB was added thereto, followed by reaction at room temperature for 5 to 10 minutes. The color reaction was terminated using a stop solution and OD was measured at 450 nm using an ELISA reader.

As a result, as shown in FIG. 4A, according to the analysis of IFN-γ ELISPOT, the vaccine prepared by mixing Lipo-Pam and Poly(I:C) induced overall higher production of IFN-γ compared to the vaccines prepared by mixing liposome and L-pampo (G2 and G3 groups). In particular, the G6 group produced significantly higher IFN-γ than other test groups, and the G8 and G9 groups also produced relatively high IFN-γ. In addition, the same formulation as the G7 group, but the addition of the sonication process before the addition of the antigen G9 group produced significantly more IFN-γ than the G7 group. In addition, the G9 group, the same formulation as the G7 group but with sonication prior to the addition of the antigen, produced significantly higher IFN-γ than the G7 group. The ELISPOT analysis of IL-4 also showed a similar tendency to the IFN-γ ELISPOT results, and the IL-4 production was high in the G6 group. When comparing the cell-mediated immune response according to whether Lipo-pam and Poly(I:C) were mixed, the production of IFN-γ and IL-4 was higher in the G6 group administered with the vaccine prepared by mixing Lipo-pam and Poly(I:C) compared to the G5 group administered with the vaccine prepared by mixing antigens with Lipo-pam alone (FIG. 4A).

As shown in FIG. 4B, according to the results of IFN-γ ELISA, the vaccine prepared by mixing Lipo-Pam and Poly(I:C) induced a large amount of IFN-γ secretion compared to the vaccine prepared by mixing liposome and L-pampo. In particular, the highest secretion of IFN-γ was induced in the G6 and G8 groups. The results of IL-4 and TNF-α ELISA also showed a similar tendency to the results of IFN-γ ELISA, and the secretion of large amounts of IL-4 and TNF-α was induced in the G6 group. When comparing the cell-mediated immune response according to whether Lipo-pam and Poly(I:C) were mixed, the secretion of IFN-γ, IL-4 and TNF-α was higher in the G6 group administered with the vaccine prepared by mixing Lipo-pam and Poly(I:C) compared to the G5 group administered with the vaccine prepared by mixing antigens with Lipo-pam alone (FIG. 4B).

Therefore, as described above, it is more important that the herpes zoster vaccine induces the cell-mediated immune response than the humoral immune response. The vaccine prepared by mixing L-pampo liposome had to undergo additional sonication, microfluidizer or extruder to uniformly disperse and stabilize the particle size of the mixture. However, the vaccine prepared by mixing Lipo-pam and Poly(I:C) was more stable and maintained the particle size over a longer period without additional processing. Therefore, it was effective to develop vaccine formulations based on Lipo-Pam which induced cell-mediated immune response better and was excellent in formulation stability.

Example 3. Confirmation of Structure of Recombinant Vaccine Prepared by Using Lipo-Pam First, to confirm the structure of the vaccine prepared by using Lipo-pam, DC-Chol (dimethylethancarbanoyl cholesterol) and DOPE (dioleoyl-phosphatidylethanolamine) lipids were stained with marina blue, Pam3-CSKKKK (SEQ. ID. NO: 2) was stained with 6-TAMRA and SE (6-Carboxytetramethylrhodamine, succinimidyl ester), and recombinant VZV gE antigen was stained with fluorescein, respectively. Lipo-Pam was prepared by the same manner as described in Example <2-1> except that DC-Chol, DOPE and Pam3-CSKKKK (SEQ. ID. NO: 2) were dissolved, DC-Chol and DOPE were mixed (3:7), and Pam3-CSKKKK (SEQ. ID. NO: 2) was added thereto at the concentration of 25 μg/dose. Then, test vaccines were prepared by mixing Lipo-Pam with Poly(I:C) at the concentration of 40 μg/dose, and adding antigens thereto at the concentration of 5 μg/dose. The structure of the vaccine was confirmed using a confocal microscope.

As a result, as shown in FIG. 5, the radius developed by the liposome lipid-stained dye was almost the same as the radius developed by the Pam3CSK-stained dye, but the radius developed by the recombinant VZV gE antigen-stained dye was larger than those. Through this, it was confirmed that the prepared vaccine had a structure in which Pam3-CSKKKK (SEQ. ID. NO: 2) and lipids formed liposome (Lipo-pam), and the recombinant VZV gE antigen was attached on the surface of liposome (FIG. 5).

Example 4. Comparison of Immunogenicity of Recombinant Vaccine According to Doses of Lipopeptide and Poly(I:C)

The immunogenicity of the recombinant vaccine was compared according to the ratio of lipids, the dose of Pam3-CSKKKK (SEQ. ID. NO: 2), the dose of Poly(I:C), and the extent of the recombinant VZV gE antigen binding to liposome.

<4-1> Preparation and Administration of Test Vaccine

Lipo-Pam was prepared by the same manner as described in Example <2-1> except that DC-Chol, DOPE and Pam3-CSKKKK (SEQ. ID. NO: 2) were dissolved, DC-Chol and DOPE were mixed (1:1 or 3:7), and Pam3-CSKKKK (SEQ. ID. NO: 2) was added thereto at the concentration of 25 or 100 μg/dose. Then, test vaccines were prepared by mixing Lipo-Pam with Poly(I:C) at the concentration of 20, 40, 60, 80 or 160 μg/dose, and adding the recombinant VZV gE antigen thereto at the concentration of 5 μg/dose. The prepared vaccines were injected intramuscularly to 6 week old C57BL/6 female mice (Orient Bio Inc., Korea) twice at two-week intervals.

TABLE 2

Preparation conditions of test vaccines for each test group

| Test Group | Composition |
|---|---|
| G1 | PBS |
| G2 | Lipo-pam(DC-Chol:DOPE(3:7) 125 μg + Pam3-CSKKKK (SEQ. ID. NO: 2) 25 μg) + Poly(I:C) 20 μg + antigen 5 μg |
| G3 | Lipo-pam(DC-Chol:DOPE(3:7) 125 μg + Pam3-CSKKKK (SEQ. ID. NO: 2) 25 μg) + Poly(I:C) 40 μg + antigen 5 μg |
| G4 | Lipo-pam(DC-Chol:DOPE(3:7) 125 μg + Pam3-CSKKKK (SEQ. ID. NO: 2) 25 μg) + Poly(I:C) 80 μg + antigen 5 μg |
| G5 | Lipo-pam(DC-Chol:DOPE(3:7) 125 μg + Pam3-CSKKKK (SEQ. ID. NO: 2) 100 μg) + Poly(I:C) 60 μg + antigen 5 μg |
| G6 | Lipo-pam(DC-Chol:DOPE(3:7) 125 μg + Pam3-CSKKKK (SEQ. ID. NO: 2) 100 μg) + Poly(I:C) 80 μg + antigen 5 μg |
| G7 | Lipo-pam(DC-Chol:DOPE(3:7) 125 μg + Pam3-CSKKKK (SEQ. ID. NO: 2) 200 μg) + Poly(I:C) 160 μg + antigen 5 μg |
| G8 | Lipo-pam(DC-Chol:DOPE(1:1) 125 μg + Pam3-CSKKKK (SEQ. ID. NO: 2) 25 μg) + Poly(I:C) 20 μg + antigen 5 μg |
| G9 | Lipo-pam(DC-Chol:DOPE(1:1) 125 μg + Pam3-CSKKKK (SEQ. ID. NO: 2) 25 μg) + Poly(I:C) 40 μg + antigen 5 μg |
| G10 | Lipo-pam(DC-Chol:DOPE(1:1) 125 μg + Pam3-CSKKKK (SEQ. ID. NO: 2) 25 μg) + Poly(I:C) 80 μg + antigen 5 μg |
| G11 | Lipo-pam(DC-Chol:DOPE(1:1) 125 μg + Pam3-CSKKKK (SEQ. ID. NO: 2) 100 μg) + Poly(I:C) 60 μg + antigen 5 μg |
| G12 | Lipo-pam(DC-Chol:DOPE(1:1) 125 μg + Pam3-CSKKKK (SEQ. ID. NO: 2) 100 μg) + Poly(I:C) 80 μg + antigen 5 μg |

<4-2> Confirmation of Binding Between Recombinant VZV gE Antigen and Lipo-Pam

The binding force between the Lipo-pam prepared in Example <4-1> and the recombinant VZV gE antigen prepared in Example 1 was confirmed by the conventional method using size-exclusion chromatography.

As a result, most of the recombinant VZV gE antigen was combined with Lipo-pam in the high Pam3-CSKKKK (SEQ. ID. NO: 2) formulations (G5 to G7, G11, and G12 groups). In addition, most of the recombinant VZV gE antigen was bound to Lipo-pam in the G2 group with low dose of Poly(I:C) competitively binding to gE antigen.

<4-3> Analysis of Humoral Immune Response

In order to analyze the humoral immune response induced by the test vaccine administered in Example <4-1>, samples were prepared by separating the sera of mice at week 0 before immunization, week 2, 2 weeks after the first vaccination and week 4, 2 weeks after the second vaccination. The total IgG antibody titer against the recombinant VZV gE antigen was analyzed by the same manner as described in Example <2-2> using the prepared samples.

As a result, as shown in FIG. 6, the total IgG antibody titer was generally higher in the case of using the Lipo-pam prepared by mixing DC-Chol and DOPE at the ratio of 3:7 (G2~G7) than in the case of using the Lipo-pam prepared by mixing DC-Chol and DOPE at the ratio of 1:1 (G8~G12). In addition, the total IgG antibody titer was induced high in proportion to the doses of Pam3-CSKKKK (SEQ. ID. NO: 2) (lipopeptide) and Poly(I:C) (FIG. 6). In particular, the total IgG antibody titer was high in the G2, G6 and G7 groups among the G2, G5, G6 and G7 groups wherein most of the recombinant VZV gE antigen was bound to Lipo-pam.

On the other hand, the total IgG antibody titers of the G2 group using Pam3-CSKKKK (SEQ. ID. NO: 2) and Poly(I:C) at the concentrations of 25 jig and 20 μg/dose and the G6 group using Pam3-CSKKKK (SEQ. ID. NO: 2) and Poly(I:C) at the concentrations of 100 jig and 80 μg/dose were similar. Therefore, it was confirmed that the optimal doses of Pam3-CSKKKK (SEQ. ID. NO: 2) and Poly(I:C) were determined according to the lipids constituting Lipo-pam or the recombinant VZV gE antigen used in the vaccine.

<4-4> Analysis of Cell-Mediated Immune Response

In order to analyze the cell-mediated immune response induced by the test vaccine administered in Example <4-1>, whole splenocytes were isolated by extracting the spleens from the mice at week 4, 2 weeks after the $2^{nd}$ vaccination. Then, the cell-mediated immune response was analyzed by ELISPOT assay and cytokine ELISA by the same manner as described in Example <2-3>.

As a result, as shown in FIG. 7A, the vaccine prepared by mixing DC-Chol and DOPE at the ratio of 3:7 produced more IFN-γ and IL-4 than the vaccine prepared by mixing DC-Chol and DOPE at the ratio of 1:1. In the case of using 25 μg/dose of Pam3-CSKKKK (SEQ. ID. NO: 2), IFN-γ and IL-4 were most produced when DC-Chol and DOPE were used at the ratio of 3:7 and Poly(I:C) was used at the concentration of 40 μg/dose. In the case of using 100 μg/dose or 200 μg/dose of Pam3-CSKKKK (SEQ. ID. NO: 2), more IFN-γ and IL-4 were produced at higher concentrations of Poly(I:C), but significantly lower IFN-γ and IL-4 were produced compared to the test group using 25 μg/dose of Pam3-CSKKKK (SEQ. ID. NO: 2) (FIG. 7A).

As shown in FIG. 7B, according to the results of cytokine ELISA, the vaccine prepared by mixing DC-Chol and DOPE at the ratio of 3:7 induced more secretion of IFN-γ and IL-4 compared to the vaccine prepared by mixing DC-Chol and DOPE at the ratio of 1:1, whereas TNF-α secretion was similar in both cases. Similar to the ELISPOT results, the vaccine with 25 μg/dose of Pam3-CSKKKK (SEQ. ID. NO: 2) induced more secretion of IFN-γ, IL-4 and TNF-α compared to the vaccine with 100 or 200 μg/dose of Pam3-CSKKKK (SEQ. ID. NO: 2). In particular, among the vaccines prepared by mixing DC-Chol and DOPE at the ratio of 3:7, the G3 group using 40 μg/dose of Poly(I:C), and among the vaccines prepared by mixing DC-Chol and DOPE at the ratio of 1:1, the G8 group using 20 μg/dose of Poly(I:C) induced the most secretion of three cytokines (FIG. 7B).

Example 5. Comparison of Immunogenicity of Recombinant Vaccine According to Doses of Lipid and Recombinant VZV gE Antigen DC-Chol:DOPE mixed at the ratio of 3:7, 25 μg/dose of Pam3-CSKKKK (SEQ. ID. NO: 2), and 20 μg/dose of Poly(I:C) were used, and the immunogenicity of the vaccine according to the doses of lipid and recombinant VZV gE antigen was compared.

<5-1> Preparation and Administration of Test Vaccine

Lipo-Pam was prepared by the same manner as described in Example <2-1> except that DC-Chol, DOPE and Pam3-CSKKKK (SEQ. ID. NO: 2) were dissolved, and DC-Chol, DOPE and Pam3-CSKKKK (SEQ. ID. NO: 2) were mixed so that the concentration of lipids (DC-Chol:DOPE=3:7) was 31.25, 62.5 or 125 μg/dose, and the concentration of Pam3-CSKKKK (SEQ. ID. NO: 2) was 25 μg/dose. Then, test vaccines were prepared by mixing Lipo-Pam with Poly(I:C) at the concentration of 20 μg/dose, and adding the recombinant VZV gE antigen thereto at the concentration of 2, 5 or 10 μg/dose, as shown in Table 3 below. The prepared vaccines were injected intramuscularly to 6 week old C57BL/6 female mice (Orient Bio Inc., Korea) twice at two-week intervals.

TABLE 3

| Preparation conditions of test vaccines for each test group | |
|---|---|
| Test Group | Composition |
| G1 | PBS |
| G2 | Lipo-pam(DC-Chol:DOPE(3:7) 31.25 μg + Pam3-CSKKKK (SEQ. ID. NO: 2) 25 μg) + Poly(I:C) 20 μg + antigen 2 μg |
| G3 | Lipo-pam(DC-Chol:DOPE(3:7) 31.25 μg + Pam3-CSKKKK (SEQ. ID. NO: 2) 25 μg) + Poly(I:C) 20 μg + antigen 5 μg |
| G4 | Lipo-pam(DC-Chol:DOPE(3:7) 31.25 μg + Pam3-CSKKKK (SEQ. ID. NO: 2) 25 μg) + Poly(I:C) 20 μg + antigen 10 μg |
| G5 | Lipo-pam(DC-Chol:DOPE(3:7) 62.5 μg + Pam3-CSKKKK (SEQ. ID. NO: 2) 25 μg) + Poly(I:C) 20 μg + antigen 2 μg |
| G6 | Lipo-pam(DC-Chol:DOPE(3:7) 62.5 μg + Pam3-CSKKKK (SEQ. ID. NO: 2) 25 μg) + Poly(I:C) 20 μg + antigen 5 μg |
| G7 | Lipo-pam(DC-Chol:DOPE(3:7) 62.5 μg + Pam3-CSKKKK (SEQ. ID. NO: 2) 25 μg) + Poly(I:C) 20 μg + antigen 10 μg |
| G8 | Lipo-pam(DC-Chol:DOPE(3:7) 125 μg + Pam3-CSKKKK (SEQ. ID. NO: 2) 25 μg) + Poly(I:C) 20 μg + antigen 2 μg |
| G9 | Lipo-pam(DC-Chol:DOPE(3:7) 125 μg + Pam3-CSKKKK (SEQ. ID. NO: 2) 25 μg) + Poly(I:C) 20 μg + antigen 5 μg |
| G10 | Lipo-pam(DC-Chol:DOPE(3:7) 125 μg + Pam3-CSKKKK (SEQ. ID. NO: 2) 25 μg) + Poly(I:C) 20 μg + antigen 10 μg |
| G11 | Lipo-pam(DC-Chol:DOPC(3:7) 125 μg + Pam3-CSKKKK (SEQ. ID. NO: 2) 25 μg) + Poly(I:C) 20 μg + antigen 5 μg |

<5-2> Analysis of Humoral Immune Response

In order to analyze the humoral immune response induced by the test vaccine administered in Example <5-1>, samples were prepared by separating the sera of mice at week 0 before immunization, week 2, 2 weeks after the first vaccination and week 4, 2 weeks after the second vaccination. The total IgG antibody titer against the recombinant VZV gE antigen was analyzed by the same manner as described in Example <2-2> using the prepared samples.

As a result, as shown in FIG. 8, it was confirmed that increasing the dose of lipids with the increase of the antigen helped the induction of antibodies. In addition, the total IgG antibody titer of the G11 group using DC-Chol and DOPC was lower than those of the other test groups (FIG. 8).

<5-3> Analysis of Cell-Mediated Immune Response

In order to analyze the cell-mediated immune response induced by the test vaccine administered in Example <5-1>, whole splenocytes were isolated by extracting the spleens from the mice at week 4, 2 weeks after the $2^{nd}$ vaccination. Then, the cell-mediated immune response was analyzed by ELISPOT assay and cytokine ELISA by the same manner as described in Example <2-3>.

As a result, as shown in FIG. 9A, according to the results of ELISPOT of IFN-γ and IL-4, the most IFN-γ and IL-4 were produced in the G8 group prepared by using 2 μg/dose of recombinant VZV gE antigen and 125 μg/dose of DC-Chol:DOPE lipids (FIG. 9A).

As shown in FIG. 9B, according to the results of cytokine ELISA, the G8 group prepared by using 2 μg/dose of recombinant VZV gE antigen and 125 μg/dose of DC-Chol: DOPE lipids induced the most secretion of three cytokines, which was similar to the results of ELISPOT assay. But, the G11 group prepared by using DC-Chol and DOPC induced less cytokine secretion than other test groups (FIG. 9B).

Example 6. Comparison of Immunogenicity of Recombinant Vaccine According to Doses of Lipid, Poly(I:C) and Recombinant VZV gE Antigen DC-Chol:DOPE mixed at the ratio of 3:7, and 25 μg/dose of Pam3-CSKKKK (SEQ. ID. NO: 2) were used, and the immunogenicity of the vaccine according to the doses of lipid, Poly(I:C) and recombinant VZV gE antigen was compared.

<6-1> Preparation and Administration of Test Vaccine

Lipo-Pam was prepared by the same manner as described in Example <2-1> except that DC-Chol, DOPE and Pam3-CSKKKK (SEQ. ID. NO: 2) were dissolved, and DC-Chol, DOPE and Pam3-CSKKKK (SEQ. ID. NO: 2) were mixed so that the concentration of lipids (DC-Chol:DOPE=3:7) was 62.5, 125 or 250 μg/dose, and the concentration of Pam3-CSKKKK (SEQ. ID. NO: 2) was 25 μg/dose. Then, test vaccines were prepared by mixing Lipo-Pam with Poly(I:C) at the concentration of 20, 40, 80 or 100 μg/dose, and adding the recombinant VZV gE antigen thereto at the concentration of 2, 5 or 10 μg/dose, as shown in Table 4 below. The prepared vaccines were injected intramuscularly to 6 week old C57BL/6 female mice (Orient Bio Inc., Korea) twice at two-week intervals.

TABLE 4

Preparation conditions of test vaccines for each test group

| Test Group | Composition |
| --- | --- |
| G1 | PBS |
| G2 | Lipo-pam(DC-Chol:DOPE(3:7) 62.5 μg + Pam3-CSKKKK (SEQ. ID. NO: 2) 25 μg) + Poly(I:C) 20 μg + antigen 2 μg |
| G3 | Lipo-pam(DC-Chol:DOPE(3:7) 62.5 μg + Pam3-CSKKKK (SEQ. ID. NO: 2) 25 μg) + Poly(I:C) 20 μg + antigen 5 μg |
| G4 | Lipo-pam(DC-Chol:DOPE(3:7) 125 μg + Pam3-CSKKKK (SEQ. ID. NO: 2) 25 μg) + Poly(I:C) 20 μg + antigen 2 μg |
| G5 | Lipo-pam(DC-Chol:DOPE(3:7) 125 μg + Pam3-CSKKKK (SEQ. ID. NO: 2) 25 μg) + Poly(I:C) 20 μg + antigen 5 μg |
| G6 | Lipo-pam(DC-Chol:DOPE(3:7) 125 μg + Pam3-CSKKKK (SEQ. ID. NO: 2) 25 μg) + Poly(I:C) 40 μg + antigen 2 μg |
| G7 | Lipo-pam(DC-Chol:DOPE(3:7) 125 μg + Pam3-CSKKKK (SEQ. ID. NO: 2) 25 μg) + Poly(I:C) 40 μg + antigen 5 μg |
| G8 | Lipo-pam(DC-Chol:DOPE(3:7) 250 μg + Pam3-CSKKKK (SEQ. ID. NO: 2) 25 μg) + Poly(I:C) 80 μg + antigen 2 μg |
| G9 | Lipo-pam(DC-Chol:DOPE(3:7) 250 μg + Pam3-CSKKKK (SEQ. ID. NO: 2) 25 μg) + Poly(I:C) 80 μg + antigen 5 μg |
| G10 | Lipo-pam(DC-Chol:DOPE(3:7) 250 μg + Pam3-CSKKKK (SEQ. ID. NO: 2) 25 μg) + Poly(I:C) 80 μg + antigen 10 μg |
| G11 | Lipo-pam(DC-Chol:DOPE(3:7) 250 μg + Pam3-CSKKKK (SEQ. ID. NO: 2) 25 μg) + Poly(I:C) 100 μg + antigen 5 μg |

<6-2> Analysis of Humoral Immune Response

In order to analyze the humoral immune response induced by the test vaccine administered in Example <6-1>, samples were prepared by separating the sera of mice at week 0 before immunization, week 2, 2 weeks after the first vaccination and week 4, 2 weeks after the second vaccination. The total IgG antibody titer against the recombinant VZV gE antigen was analyzed by the same manner as described in Example <2-2> using the prepared samples.

As a result, as shown in FIG. 10, when Lipo-pam was prepared by using 62.5 μg/dose of lipid and 20 μg/dose of Poly(I:C), the total IgG antibody titer was similar between the G2 group prepared by using 2 μg/dose of the recombinant VZV gE antigen and the G3 group prepared by using 5 μg/dose of the recombinant VZV gE antigen. When Lipo-pam was prepared by using 250 μg/dose of lipid and 80 μg/dose of Poly(I:C), the total IgG antibody titer was similar between the G8 group prepared by using 2 μg/dose of the recombinant VZV gE antigen, the G9 group prepared by using 5 μg/dose of the recombinant VZV gE antigen and the G10 group prepared by using 10 μg/dose of the recombinant VZV gE antigen (FIG. 10). In the isotype analysis, the ratio of IgG2b/IgG1 was higher in the G8, G9, G2, and G6 groups, and the ratio of IgG2c/IgG1 was higher in the G8, G6, and G9 groups than in the other test groups.

<6-3> Analysis of Cell-Mediated Immune Response

In order to analyze the cell-mediated immune response induced by the test vaccine administered in Example <6-1>, whole splenocytes were isolated by extracting the spleens from the mice at week 4, 2 weeks after the $2^{nd}$ vaccination. Then, the cell-mediated immune response was analyzed by ELISPOT assay and cytokine ELISA by the same manner as described in Example <2-3>.

As a result, as shown in FIG. 11A, according to the results of ELISPOT of IFN-γ and IL-4, the most IFN-γ and IL-4 were produced in the G6 group using 2 μg/dose of recombinant VZV gE antigen and Lipo-pam prepared by using 125 μg/dose of lipid and 40 μg/dose of Poly(I:C) (FIG. 11A).

As shown in FIG. 11B, according to the results of cytokine ELISA, the G6 group using 2 μg/dose of recombinant VZV gE antigen and Lipo-pam prepared by using 125 μg/dose of lipid and 40 μg/dose of Poly(I:C) induced the most secretion of IFN-γ, IL-4 and TNF-α (FIG. 11B).

Example 7. Comparison of Immunogenicity of Attenuated Herpes Zoster Vaccine and Recombinant Vaccine According to Dose of Antigen The immunogenicity of Zostavax, the commercially available attenuated live vaccine, and the recombinant vaccine prepared by using the recombinant VZV gE antigen according to the dose of the antigen included in the recombinant vaccine was compared.

<7-1> Preparation and Administration of Test Vaccine

Lipo-Pam was prepared by the same manner as described in Example <2-1> except that DC-Chol, DOPE and Pam3-CSKKKK (SEQ. ID. NO: 2) were dissolved, and DC-Chol, DOPE and Pam3-CSKKKK (SEQ. ID. NO: 2) were mixed so that the concentration of lipids (DC-Chol:DOPE 3:7) was 125 μg/dose, and the concentration of Pam3-CSKKKK (SEQ. ID. NO: 2) was 25 μg/dose. In addition, L-pampo was prepared by mixing 25 μg/dose of Pam3-CSKKKK (SEQ. ID. NO: 2), 200 μg/dose of Poly(I:C) and 5 μg/dose of antigen, which was used as the control. Thereafter, test vaccines having the compositions as described in Table 5 below were prepared. Zostavax or the prepared vaccines were injected intramuscularly to 6 week old C57BL/6 female mice (Orient Bio Inc., Korea) twice at two-week intervals.

TABLE 5

Preparation conditions of test vaccines for each test group

| Test Group | Composition |
| --- | --- |
| G1 | PBS |
| G2 | Zostavax (attenuated herpes zoster live vaccine 1940 PFU, ¹/₁₀ of the amount administered to a person) |

TABLE 5-continued

Preparation conditions of test vaccines for each test group

| Test Group | Composition |
|---|---|
| G3 | aluminum hydroxide 100 μg + antigen 5 μg |
| G4 | L-Pampo(Pam3-CSKKKK (SEQ. ID. NO: 2) 25 μg + Poly(I:C) 200 μg) + antigen 5 μg |
| G5 | Lipo-pam(DC-Chol:DOPE(3:7) 125 μg + Pam3-CSKKKK (SEQ. ID. NO: 2) 25 μg) + Poly(I:C) 40 μg + antigen 2 μg |
| G6 | Lipo-pam(DC-Chol:DOPE(3:7) 125 μg + Pam3-CSKKKK (SEQ. ID. NO: 2) 25 μg) + Poly(I:C) 40 μg + antigen 5 μg |

<7-2> Analysis of Humoral Immune Response

In order to analyze the humoral immune response induced by the test vaccine administered in Example <7-1>, samples were prepared by separating the sera of mice at week 0 before immunization, week 2, 2 weeks after the first vaccination and week 4, 2 weeks after the second vaccination. The total IgG antibody titer against the recombinant VZV gE antigen and the isotype thereof were analyzed by the same manner as described in Example <2-2> using the prepared samples.

As a result, as shown in FIG. 12, the G2 group treated with Zostavax and the G3 group using aluminum hydroxide showed lower total IgG antibody levels than the G4, G5 and G6 groups using L-pampo or Lipo-Pam (FIG. 12). In isotype analysis, most IgG1 type antibodies were formed in the G3 group using aluminum hydroxide, and the ratio of IgG2b/IgG1 and IgG2c/IgG1 was higher in the G5 and G6 groups using Lipo-pam than in the G4 group using L-pampo.

<7-3> Analysis of Cell-Mediated Immune Response

In order to analyze the cell-mediated immune response induced by the test vaccine administered in Example <7-1>, whole splenocytes were isolated by extracting the spleens from the mice at week 4, 2 weeks after the $2^{nd}$ vaccination. Then, ELISPOT assay and cytokine ELISA were performed by the same manner as described in Example <2-3> using the splenocytes. The cell-mediated immune response was analyzed by comparing the levels of CD4+ T cells secreting cytokines specific to the recombinant VZV gE antigen in each formulation by performing intracellular cytokine staining (ICS) analysis for IFN-γ, TNF-α and IL-2 using a flow cytometer.

As a result, as shown in FIG. 13A, according to the results of ELISPOT of IFN-γ and IL-4, significantly lower IFN-γ and IL-4 were produced in the G2 group administered with Zostavax, while the most IFN-γ and IL-4 were produced in the G5 and G6 groups using Lipo-pam (FIG. 13A).

As shown in FIG. 11B, according to the results of cytokine ELISA, the least secretion of IFN-γ, IL-4 and TNF-α was induced in the G2 group administered with Zostavax, while the most secretion of IFN-γ, IL-4 and TNF-α was induced in the G5 and G6 groups using Lipo-pam (FIG. 13B).

As shown in FIG. 14, the trend of cytokines secreted in each test group showed high frequency of CD4+ T cells secreting each cytokine in the G5 and G6 groups using Lipo-pam (FIG. 14).

In addition, as shown in FIG. 15, according to the results of comparing the polyfunctionality of gE antigen-specific CD4+ T cells assuming 100% of the cells that secrete one or more types of cytokines in each test group, the test groups with high T cells secreting all three cytokines among the CD4+ T cells secreting one or more cytokines were the G5 and G6 groups using Lipo-pam. On the other hand, the G2 group administered with Zostavax and the G3 group using aluminum hydroxide showed high ratio of CD4+ T cells that secrete only one cytokine, confirming low multifunctionality (FIG. 15).

Example 8. Comparison of Immunogenicity of Attenuated Herpes Zoster Vaccine and Recombinant Vaccine According to Doses of Lipid and Poly(I:C)

The immunogenicity of Zostavax, the commercially available attenuated live vaccine, and the recombinant vaccine prepared by using the recombinant VZV gE antigen according to the doses of the lipid and Poly(I:C) included in the recombinant vaccine was compared.

<8-1> Preparation and Administration of Test Vaccine

Lipo-Pam was prepared by the same manner as described in Example <2-1> except that DC-Chol, DOPE and Pam3-CSKKKK (SEQ. ID. NO: 2) were dissolved, and DC-Chol, DOPE and Pam3-CSKKKK (SEQ. ID. NO: 2) were mixed so that the concentration of lipids (DC-Chol:DOPE 3:7) was 125 μg/dose, and the concentration of Pam3-CSKKKK (SEQ. ID. NO: 2) was 25 μg/dose or the concentration of lipids (DC-Chol:DOPE=1:1) was 125 μg/dose, and the concentration of Pam3-CSKKKK (SEQ. ID. NO: 2) was 25 μg/dose. In addition, L-pampo was prepared by mixing 25 μg/dose of Pam3-CSKKKK (SEQ. ID. NO: 2), 200 μg/dose of Poly(I:C) and 5 μg/dose of antigen. DC-Chol:DOPE liposome was prepared by the same manner as described in Example <2-1>. Then, test vaccines were prepared by mixing Lipo-Pam with Poly(I:C) at the concentration of 20, 40 or 80 μg/dose, and adding the recombinant VZV gE antigen thereto at the concentration of 5 μg/dose (G6~G9 groups), by simultaneously mixing Lipo-Pam with Poly(I:C) at the concentration of 40 μg/dose and the recombinant VZV gE antigen at the concentration of 5 μg/dose (G10 and G 11), by mixing Lipo-Pam with DC-Chol:DOPE liposome (G5 group), or by mixing 100 μg/dose of aluminum hydroxide and 5 μg/dose of recombinant VZV gE antigen. Zostavax or the prepared vaccines were injected intramuscularly to 6 week old C57BL/6 female mice (Orient Bio Inc., Korea) twice at two-week intervals.

TABLE 6

Preparation conditions of test vaccines for each test group

| Test Group | Composition |
|---|---|
| G1 | PBS |
| G2 | aluminum hydroxide 100 μg + antigen 5 μg |
| G3 | Zostavax(attenuated herpes zoster live vaccine 1940 PFU, 1/10 of the amount administered to a person) |
| G4 | L-Pampo(Pam3-CSKKKK (SEQ. ID. NO: 2) 25 μg + Poly(I:C) 200 μg) + antigen 5 μg |
| G5 | liposome(DC-Chol:DOPE(3:7) 125 μg) + L-Pampo(Pam3-CSKKKK (SEQ. ID. NO: 2) 25 μg + Poly(I:C) 200 μg) + antigen 5 μg/sonication |
| G6 | Lipo-pam(DC-Chol:DOPE(3:7) 125 μg + Pam3-CSKKKK (SEQ. ID. NO: 2) 25 μg) + Poly(I:C) 40 μg + antigen 5 μg |
| G7 | Lipo-pam(DC-Chol:DPPC(1:1) 125 μg + Pam3-CSKKKK (SEQ. ID. NO: 2) 25 μg) + Poly(I:C) 40 μg + antigen 5 μg |
| G8 | Lipo-pam(DC-Chol:DPPC(1:1) 125 μg + Pam3-CSKKKK (SEQ. ID. NO: 2) 25 μg) + Poly(I:C) 20 μg + antigen 5 μg |
| G9 | Lipo-pam(DC-Chol:DOPE(1:1) 125 μg + Pam3-CSKKKK (SEQ. ID. NO: 2) 25 μg) + Poly(I:C) 80 μg + antigen 5 μg |
| G10 | Lipo-pam(DC-Chol:DOPE(3:7) 125 μg + Pam3-CSKKKK (SEQ. ID. NO: 2) 25 μg) + [Poly(I:C) 40 μg + antigen 5 μg] |
| G11 | Lipo-pam(DC-Chol:DOPE(1:1) 125 μg + Pam3-CSKKKK (SEQ. ID. NO: 2) 25 μg) + [Poly(I:C) 40 μg + antigen 5 μg] |

<8-2> Analysis of Humoral Immune Response

In order to analyze the humoral immune response induced by the test vaccine administered in Example <8-1>, samples were prepared by separating the sera of mice at week 0 before immunization, week 2, 2 weeks after the first vaccination and week 4, 2 weeks after the second vaccination. The antibody titer was determined by analysis of antigen-specific antibody formation by ELISA using the prepared samples. The total IgG antibody titer against the recombinant VZV gE antigen was analyzed by the same manner as described in Example <2-2>.

As a result, as shown in FIG. 16, the G3 group treated with Zostavax and the G2 group using aluminum hydroxide showed lower total IgG antibody titer than the G4 to G11 groups using L-pampo or Lipo-Pam (FIG. 16).

<8-3> Analysis of Cell-Mediated Immune Response

In order to analyze the cell-mediated immune response induced by the test vaccine administered in Example <8-1>, whole splenocytes were isolated by extracting the spleens from the mice at week 4, 2 weeks after the $2^{nd}$ vaccination. Then, the cell-mediated immune response was analyzed by ELISPOT assay and cytokine ELISA by the same manner as described in Example <2-3>.

As a result, as shown in FIG. 17A, according to the results of ELISPOT of IFN-γ and IL-4, significantly lower IFN-γ and IL-4 were produced in the G3 group administered with Zostavax, while many IFN-γ and IL-4 were produced in the G7 group using 40 μg/dose of Poly(I:C) and Lipo-pam prepared by using DC-Chol:DPPC (1:1) and the G11 group using Lipo-Pam, 40 μg/dose of Poly(I:C) and 5 μg/dose of recombinant VZV gE antigen (FIG. 17A).

As shown in FIG. 17B, according to the results of cytokine ELISA, the most secretion of IFN-γ was induced in the G7 group using 40 μg/dose of Poly(I:C) and Lipo-pam prepared by using DC-Chol:DPPC (1:1) and the G5 group using DC-Chol:DOPE liposome and L-pampo. In addition, the secretion of IL-4 was not significantly different between the formulations, but much secretion was induced in the G7 to G9 and G11 groups using Lipo-pam prepared by using DC-Chol:DPPC (1:1). TNF-α was induced a lot in the G5, G7, G9 and G11 groups (FIG. 17B).

Example 9. Comparison of Immunogenicity of Recombinant Vaccine According to Type of Lipid, Dose of Poly(I:C) and Method of Recombinant VZV gE Antigen Mixing The immunogenicity of the vaccine according to the type of lipid, the dose of Poly(I:C), and the method of mixing the recombinant VZV gE antigen in the preparation of Lipo-pam was compared.

<9-1> Preparation and Administration of Test Vaccine

Lipo-Pam was prepared by the same manner as described in Example <2-1> except that DC-Chol, DOPE and Pam3-CSKKKK (SEQ. ID. NO: 2) were dissolved, and DC-Chol, DOPE and Pam3-CSKKKK (SEQ. ID. NO: 2) were mixed so that the concentration of lipids (DC-Chol:DOPE 3:7) was 125 μg/dose, and the concentration of Pam3-CSKKKK (SEQ. ID. NO: 2) was 25 μg/dose or the concentration of lipids (DC-Chol:DPPC=1:1 or 3:7) was 125 μg/dose, and the concentration of Pam3-CSKKKK (SEQ. ID. NO: 2) was 25 μg/dose. In addition, L-pampo was prepared by mixing 25 μg/dose of Pam3-CSKKKK (SEQ. ID. NO: 2), 200 μg/dose of Poly(I:C) and 5 μg/dose of recombinant VZV gE antigen. Then, test vaccines were prepared by mixing Lipo-Pam with Poly(I:C) at the concentration of 40 or 200 μg/dose, and adding the recombinant VZV gE antigen thereto at the concentration of 5 μg/dose (G3~G6 groups), or by simultaneously mixing Lipo-Pam with poly(I:C) at the concentration of 40 or 200 μg/dose and the recombinant VZV gE antigen at the concentration of 5 μg/dose (G7 G10 groups). The prepared vaccines were injected intramuscularly to 6 week old C57BL/6 female mice (Orient Bio Inc., Korea) twice at two-week intervals.

TABLE 7

Preparation conditions of test vaccines for each test group

| Test Group | Composition |
|---|---|
| G1 | PBS |
| G2 | L-Pampo(Pam3-CSKKKK (SEQ. ID. NO: 2) 25 μg + Poly(I:C) 200 μg) + antigen 5 μg |
| G3 | Lipo-pam(DC-Chol:DOPE(3:7) 125 μg + Pam3-CSKKKK (SEQ. ID. NO: 2) 25 μg) + Poly(I:C) 40 μg + antigen 5 μg |
| G4 | Lipo-pam(DC-Chol:DPPC(3:7) 125 μg + Pam3-CSKKKK (SEQ. ID. NO: 2) 25 μg) + Poly(I:C) 40 μg + antigen 5 μg |
| G5 | Lipo-pam(DC-Chol:DPPC(3:7) 125 μg + Pam3-CSKKKK (SEQ. ID. NO: 2) 25 μg) + Poly(I:C) 200 μg + antigen 5 μg |
| G6 | Lipo-pam(DC-Chol:DPPC(1:1) 125 μg + Pam3-CSKKKK (SEQ. ID. NO: 2) 25 μg) + Poly(I:C) 40 μg + antigen 5 μg |
| G7 | Lipo-pam(DC-Chol:DOPE(3:7) 125 μg + Pam3-CSKKKK (SEQ. ID. NO: 2) 25 μg) + [Poly(I:C) 40 μg + antigen 5 μg] |
| G8 | Lipo-pam(DC-Chol:DPPC(3:7) 125 μg + Pam3-CSKKKK (SEQ. ID. NO: 2) 25 μg) + [Poly(I:C) 40 μg + antigen 5 μg] |
| G9 | Lipo-pam(DC-Chol:DPPC(3:7) 125 μg + Pam3-CSKKKK (SEQ. ID. NO: 2) 25 μg) + [Poly(I:C) 200 μg + antigen 5 μg] |
| G10 | Lipo-pam(DC-Chol:DPPC(1:1) 125 μg + Pam3-CSKKKK (SEQ. ID. NO: 2) 25 μg) + [Poly(I:C) 40 μg + antigen 5 μg] |

<9-2> Analysis of Humoral Immune Response

In order to analyze the humoral immune response induced by the test vaccine administered in Example <9-1>, samples were prepared by separating the sera of mice at week 0 before immunization, week 2, 2 weeks after the first vaccination and week 4, 2 weeks after the second vaccination. The total IgG antibody titer against the recombinant VZV gE antigen was analyzed by the same manner as described in Example <2-2> using the prepared samples.

As a result, as shown in FIG. 18, there was no difference in the total IgG antibody titer by the type of lipid and the method of mixing Poly(I:C) and antigen (FIG. 18). In isotype analysis, the ratio of IgG2b/IgG1 and IgG2c/IgG1 was higher in the G4 to G6 groups using DC-Chol:DPPC at the ratio of 3:7 or 1:1 than in the other groups.

<9-3> Analysis of Cell-Mediated Immune Response

In order to analyze the cell-mediated immune response induced by the test vaccine administered in Example <9-1>, whole splenocytes were isolated by extracting the spleens from the mice at week 4, 2 weeks after the $2^{nd}$ vaccination. Then, the cell-mediated immune response was analyzed by ELISPOT assay and cytokine ELISA by the same manner as described in Example <2-3>.

As a result, as shown in FIG. 19A, according to the results of ELISPOT of IFN-γ, more IFN-γ was produced in the G4 to G6 and G8 to G10 groups using Lipo-pam prepared by using DC-Chol:DPPC than in the G2 group using L-pampo and the G3 and G7 groups using DC-Chol:DOPE. According to the results of IL-4 ELISPOT, IL-4 was produced at similar levels in all test groups (FIG. 19A).

As shown in FIG. 19B, according to the results of cytokine ELISA, the most secretion of IFN-γ and TNF-α was induced by the formulation using DC-Chol:DPPC than the formulation using DC-Chol:DOPE. The secretion of IFN-γ and TNF-α was most induced in the G6 and G10 groups using DC-Chol:DPPC at the ratio of 1:1. IL-4 was more secreted in the G2 group using L-pampo and in the G6 and G10 groups using DC-Chol:DPPC at the ratio of 1:1. Similar levels of IL-4 were induced in the G3 and G7 groups using DC-Chol:DOPE as in the group using DC-Chol:DPPC (FIG. 19B).

Example 10. Comparison of Immunogenicity of Recombinant Vaccine According to Type and Dose of Lipid, Kind of Immunoactive Substance and Dose of Recombinant VZV gE Antigen The immunogenicity of the vaccine according to the type and dose of lipid, the kind of immunoactive substance and the dose of recombinant VZV gE antigen was compared. As the immunoactive substance, Poly(I:C) or QS21 was used.

<10-1> Preparation and Administration of Test Vaccine

Lipo-Pam was prepared by the same manner as described in Example <2-1> except that DC-Chol, DOPE, DPPC and Pam3-CSKKKK (SEQ. ID. NO: 2) were dissolved, and DC-Chol, DPPC and Pam3-CSKKKK (SEQ. ID. NO: 2) were mixed so that the concentration of lipids (DC-Chol:DOPE 3:7) was 125 μg/dose, and the concentration of Pam3-CSKKKK (SEQ. ID. NO: 2) was 25 μg/dose or the concentration of lipids (DC-Chol:DPPC=1:1) was 62.5, 125 or 250 μg/dose, and the concentration of Pam3-CSKKKK (SEQ. ID. NO: 2) was 25 μg/dose. In addition, L-pampo was prepared by mixing 25 μg/dose of Pam3-CSKKKK (SEQ. ID. NO: 2), 200 μg/dose of Poly(I:C) and 5 μg/dose of recombinant VZV gE antigen. Then, test vaccines were prepared by mixing Lipo-Pam with Poly(I:C) at the concentration of 40 μg/dose (G2~G8 groups), or by mixing Lipo-Pam with QS21 at the concentration of 5 μg/dose (G9) and adding the recombinant VZV gE antigen thereto at the concentration of 5 μg/dose. The prepared vaccines were injected intramuscularly to 6 week old C57BL/6 female mice (Orient Bio Inc., Korea) twice at two-week intervals.

TABLE 8

Preparation conditions of test vaccines for each test group

| Test Group | Composition |
|---|---|
| G1 | PBS |
| G2 | Lipo-pam(DC-Chol:DOPE(3:7) 125 μg + Pam3-CSKKKK (SEQ. ID. NO: 2) 25 μg) + Poly(I:C) 40 μg + antigen 5 μg |
| G3 | Lipo-pam(DC-Chol:DPPC(1:1) 62.5 μg + Pam3-CSKKKK (SEQ. ID. NO: 2) 25 μg) + Poly(I:C) 40 μg + antigen 2 μg |
| G4 | Lipo-pam(DC-Chol:DPPC(1:1) 62.5 μg + Pam3-CSKKKK (SEQ. ID. NO: 2) 25 μg) + Poly(I:C) 40 μg + antigen 5 μg |
| G5 | Lipo-pam(DC-Chol:DPPC(1:1) 125 μg + Pam3-CSKKKK (SEQ. ID. NO: 2) 25 μg) + Poly(I:C) 40 μg + antigen 2 μg |
| G6 | Lipo-pam(DC-Chol:DPPC(1:1) 125 μg + Pam3-CSKKKK (SEQ. ID. NO: 2) 25 μg) + Poly(I:C) 40 μg + antigen 5 μg |
| G7 | Lipo-pam(DC-Chol:DPPC(1:1) 250 μg + Pam3-CSKKKK (SEQ. ID. NO: 2) 25 μg) + Poly(I:C) 40 μg + antigen 2 μg |
| G8 | Lipo-pam(DC-Chol:DPPC(1:1) 250 μg + Pam3-CSKKKK (SEQ. ID. NO: 2) 25 μg) + Poly(I:C) 40 μg + antigen 5 μg |
| G9 | Lipo-pam(DC-Chol:DPPC(1:1) 125 μg + Pam3-CSKKKK (SEQ. ID. NO: 2) 25 μg) + QS21 5 μg + antigen 5 μg |

<10-2> Analysis of Humoral Immune Response

In order to analyze the humoral immune response induced by the test vaccine administered in Example <10-1>, samples were prepared by separating the sera of mice at week 0 before immunization, week 2, 2 weeks after the first vaccination and week 4, 2 weeks after the second vaccination. The total IgG antibody titer against the recombinant VZV gE antigen was analyzed by the same manner as described in Example <2-2> using the prepared samples.

As a result, as shown in FIG. 20, the total antibody titer according to the type of lipid was the highest in the G2 group using Lipo-pam prepared by using DC-Chol and DOPE, and the high antibody formation was induced in the G9 group using QS21 instead of Poly(I:C) as an immunoactive substance (FIG. 20).

<10-3> Analysis of Cell-Mediated Immune Response

In order to analyze the cell-mediated immune response induced by the test vaccine administered in Example <10-1>, whole splenocytes were isolated by extracting the spleens from the mice at week 4, 2 weeks after the $2^{nd}$ vaccination. Then, the cell-mediated immune response was analyzed by ELISPOT assay and cytokine ELISA by the same manner as described in Example <2-3>.

As a result, as shown in FIG. 21A, according to the results of ELISPOT of IFN-γ, more IFN-γ was produced in the group using DC-Chol and DPPC as lipids than in the G2 group using DC-Chol and DOPE as lipids. IFN-γ was produced most in the G9 group using Lipo-pam prepared by using DC-Chol and DPPC as lipids and using QS21 as an immunoactive substance. In addition, according to the results of ELISPOT of IL-4, more IL-4 was produced in the group using DC-Chol and DPPC as lipids than in the G2 group using DC-Chol and DOPE as lipids. IL-4 was produced at similar levels in the G6 group using 40 μg/dose of Poly(I:C) and 5 μg/dose of recombinant VZV gE antigen and the G9 group using 5 μg/dose of QS21 and 5 μg/dose of recombinant VZV gE antigen (FIG. 21A).

As shown in FIG. 21B, according to the results of cytokine ELISA, more secretion of IFN-γ, IL-4 and TNF-α was induced in the G3~G8 groups using DC-Chol:DPPC than in the G2 group using DC-Chol:DOPE as lipids. More secretion of IFN-γ and TNF-α was induced in the G9 group using 5 μg/dose of QS21 and 5 μg/dose of recombinant VZV gE antigen than in the G6 group using 40 μg/dose of Poly(I:C) and 5 μg/dose of recombinant VZV gE antigen. Secretion of IL-4 was induced at similar levels in both groups (FIG. 21B).

Therefore, it was confirmed from the results of <Example 10> that the use of QS21 as well as Poly(I:C) as an immunoactive substance in the preparation of Lipo-pam induced humoral and cell-mediated immune responses, so that the vaccine efficacy was improved.

Example 11. Comparison of Immunogenicity of Recombinant Vaccine According to Kind of Lipopeptide The immunogenicity of the vaccine according to the type of lipopeptide included in the recombinant vaccine prepared by using the recombinant VZV gE antigen was compared.

<11-1> Preparation and Administration of Test Vaccine

Lipo-Pam was prepared by the same manner as described in Example <2-1> except that DC-Chol, DPPC and lipopeptide were dissolved, and DC-Chol, DPPC and lipopeptide were mixed so that the concentration of lipids (DC-Chol:DPPC=1:1) was 125 μg/dose, and the concentration of lipopeptide was 25 μg/dose. The size and zeta potential of Lipo-Pam were measured using a particle size analyzer (Malvern, Nono-ZS). At this time, Pam3-CSKKKK (SEQ. ID. NO: 2), Dhc-SKKKK (SEQ. ID. NO: 3), PamDhc-SKKKK (SEQ. ID. NO: 3), Pam-CSKKKK (SEQ. ID. NO: 2), Pam2Cys-SKKKK (SEQ. ID. NO: 3), PHC-SKKKK (SEQ. ID. NO: 3) or FSL-1 (i.e., Pam2CGDPKHPKSF; SEQ. ID. NO: 4) was used as the lipopeptide.

Then, test vaccines were prepared by mixing Lipo-Pam with Poly(I:C) at the concentration of 40 μg/dose and adding the recombinant VZV gE antigen thereto at the concentration of 5 μg/dose. The size and zeta potential of the test vaccine composition were measured using a particle size analyzer (Malvern, Nono-ZS).

TABLE 9

Size and zeta potential of Lipo-Pam according to type of lipopeptide

| Lipopeptide inserted in Lipo-Pam | Size (nm) | Particle distribution index (PDI) | Zeta potential (mV) |
| --- | --- | --- | --- |
| Pam3-CSKKKK (SEQ. ID. NO: 2) | 96.49 | 0.1465 | 27.2 |
| Dhc-SKKKK (SEQ. ID. NO: 3) | 116.4 | 0.217 | 56.1 |
| PamDhc-SKKKK (SEQ. ID. NO: 3) | 98.46 | 0.218 | 59.1 |
| Pam-CSKKKK (SEQ. ID. NO: 2) | 89.05 | 0.151 | 42.9 |
| Pam2Cys-SKKKK (SEQ. ID. NO: 3) | 97.74 | 0.222 | 54.4 |
| PHC-SKKKK (SEQ. ID. NO: 3) | 95.96 | 0.206 | 50.3 |
| FSL-1 | 125.9 | 0.168 | 37.8 |

TABLE 10

Size and zeta potential of recombinant vaccine according to type of lipopeptide

| Lipopeptide used in vaccine preparation | Size (nm) | Particle distribution index (PDI) | Zeta potential (mV) |
| --- | --- | --- | --- |
| Pam3-CSKKKK (SEQ. ID. NO: 2) + Poly(I:C) + antigen | 211.9 | 0.191 | −53.7 |
| Dhc-SKKKK (SEQ. ID. NO: 3) + Poly(I:C) + antigen | 128.0 | 0.163 | −38.8 |
| PamDhc-SKKKK (SEQ. ID. NO: 3) + Poly(I:C) + antigen | 180.5 | 0.156 | −28.5 |
| Pam-CSKKKK (SEQ. ID. NO: 2) + Poly(I:C) + antigen | 207.8 | 0.182 | −30.2 |
| Pam2Cys-SKKKK (SEQ. ID. NO: 3) + Poly(I:C) + antigen | 138.6 | 0.180 | −34.5 |
| PHC-SKKKK (SEQ. ID. NO: 3) + Poly(I:C) + antigen | 122.2 | 0.178 | −35.0 |
| FSL-1 + Poly(I:C) + antigen | 276.0 | 0.273 | −35.2 |

As a result, as shown in Table 9, Lipo-Pam properly produced recombinant vaccines without precipitates, which were 90-130 nm in size (Table 9). In addition, as shown in Table 10, the vaccine composition comprising lipopeptide, Poly(I:C) and antigen formed recombinant vaccines with the size of 120 to 300 nm (Table 10).

Then, the prepared vaccines were injected intramuscularly to 6 week old C57BL/6 female mice (Orient Bio Inc., Korea) twice at two-week intervals as shown in Table 11 below.

TABLE 11

Preparation conditions of test vaccines for each test group

| Test Group | Composition |
| --- | --- |
| G1 | PBS |
| G2 | Zostavax(attenuated herpes zoster live vaccine 1940 PFU, 1/10 of the amount administered to a person) |
| G3 | Lipo-pam(DC-Chol:DPPC(1:1) 125 μg + Pam3-CSKKKK (SEQ. ID. NO: 2) 25 μg) + Poly(I:C) 40 μg + antigen 5 μg |
| G4 | Lipo-pam(DC-Chol:DPPC(1:1) 125 μg + Dhc-SKKKK (SEQ. ID. NO: 3) 25 μg) + Poly(I:C) 40 μg + antigen 5 μg |
| G5 | Lipo-pam(DC-Chol:DPPC(1:1) 125 μg + PamDhc-SKKKK (SEQ. ID. NO: 3) 25 μg) + Poly(I:C) 40 μg + antigen 5 μg |
| G6 | Lipo-pam(DC-Chol:DPPC(1:1) 125 μg + Pam-CSKKKK (SEQ. ID. NO: 2) 25 μg) + Poly(I:C) 40 μg + antigen 5 μg |
| G7 | Lipo-pam(DC-Chol:DPPC(1:1) 125 μg + Pam2Cys-SKKKK (SEQ. ID. NO: 3) 25 μg) + Poly(I:C) 40 μg + antigen 5 μg |
| G8 | Lipo-pam(DC-Chol:DPPC(1:1) 125 μg + PHC-SKKKK (SEQ. ID. NO: 3) 25 μg) + Poly(I:C) 40 μg + antigen 5 μg |
| G9 | Lipo-pam(DC-Chol:DPPC(1:1) 125 μg + FSL-1 25 μg) + Poly(I:C) 40 μg + antigen 5 μg |

<11-2> Analysis of Humoral Immune Response

In order to analyze the humoral immune response induced by the test vaccine administered in Example <11-1>, samples were prepared by separating the sera of mice at week 0 before immunization, week 2, 2 weeks after the first vaccination and week 4, 2 weeks after the second vaccination. The total IgG antibody titer against the recombinant VZV gE antigen was analyzed by the same manner as described in Example <2-2> using the prepared samples.

As a result, as shown in FIG. 22, antibodies were generated in all the test groups, in particular, higher antibody titers were induced in the G3, G7 and G9 groups using Lipo-pam prepared by using Pam3-CSKKKK (SEQ. ID. NO: 2), Pam2Cys-SKKKK (SEQ. ID. NO: 3) and FSL-1 as lipopeptides compared to other test groups (FIG. 22).

<11-3> Analysis of Cell-Mediated Immune Response

In order to analyze the cell-mediated immune response induced by the test vaccine administered in Example <11-1>, whole splenocytes were isolated by extracting the spleens from the mice at week 4, 2 weeks after the $2^{nd}$ vaccination. Then, the cell-mediated immune response was analyzed by ELISPOT assay and cytokine ELISA by the same manner as described in Example <2-3>.

As a result, as shown in FIG. 23A, according to the results of ELISPOT of IFN-γ, antibodies were generated in all the test groups, in particular, IFN-γ was well produced in the G3, G4, G6 and G8 groups using Lipo-pam prepared by using Pam3-CSKKKK (SEQ. ID. NO: 2), Dhc-SKKKK (SEQ. ID. NO: 3), Pam-CSKKKK (SEQ. ID. NO: 2) or PHC-SKKKK (SEQ. ID. NO: 3) as lipopeptide. In addition, according to the results of IL-4 ELISPOT, IL-4 was well produced in the G3, G4, G7 and G8 groups using Pam3-CSKKKK (SEQ. ID. NO: 2), Dhc-SKKKK (SEQ. ID. NO: 3), Pam2Cys-SKKKK (SEQ. ID. NO: 3) or PHC-SKKKK (SEQ. ID. NO: 3) as lipopeptide (FIG. 23A).

As shown in FIG. 23B, according to the results of cytokine ELISA, more secretion of IFN-γ, IL-4 and TNF-α was induced in the G3 and G4 groups using Pam3-CSKKKK (SEQ. ID. NO: 2) or Dhc-SKKKK (SEQ. ID. NO: 3) as lipopeptide.

Therefore, it was confirmed from the results of <Example 11> that any type of lipopeptide used in the preparation of Lipo-pam induced humoral and cell-mediated immune responses, so that the Lipo-pam according to the present invention can be used for the preparation of vaccines using a combination of antigens and various types of lipopeptides. In particular, in the preparation of a recombinant herpes zoster vaccine, Pam3-CSKKKK (SEQ. ID. NO: 2), which induces both humoral and cell-mediated immune responses, can be used as lipopeptide to improve the vaccine efficacy.

Example 12. Comparison of Immunogenicity of Recombinant Vaccine Formulated with L-Pampo or Lipo-Pam Against Japanese Encephalitis Virus gE Antigen The immunogenicity of the recombinant vaccine formulated with L-pampo or Lipo-pam was compared using recombinant Japanese encephalitis virus gE antigen.

<12-1> Preparation and Administration of Test Vaccine

Lipo-Pam was prepared by the same manner as described in Example <2-1> except that DC-Chol, DOPE and Pam3-CSKKKK (SEQ. ID. NO: 2) were dissolved, and DC-Chol, DOPE and Pam3-CSKKKK (SEQ. ID. NO: 2) were mixed so that the concentration of lipids (DC-Chol:DOPE 3:7) was 125 μg/dose, and the concentration of Pam3-CSKKKK (SEQ. ID. NO: 2) was 25 μg/dose. L-pampo was prepared by mixing 25 μg/dose of Pam3-CSKKKK (SEQ. ID. NO: 2), 20 μg/dose of Poly(I:C), and 0.1 or 0.5 μg/dose of recombinant JEV gE antigen. The recombinant JEV gE antigen was expressed in a baculovirus-insect cell system and purified. Then, test vaccines were prepared by mixing Lipo-Pam with Poly(I:C) at the concentration of 40 μg/dose and adding the recombinant JEV gE antigen thereto at the concentration of 0.1 or 0.5 μg/dose. The prepared vaccines were injected intramuscularly to 6 week old C57BL/6 female mice (Orient Bio Inc., Korea) twice at two-week intervals.

TABLE 12

Preparation conditions of test vaccines for each test group

| Test Group | Composition |
|---|---|
| G1 | PBS |
| G2 | Inactivated JEV antigen 0.1 μg/dose |
| G3 | Inactivated JEV antigen 0.5 μg/dose |
| G4 | L-Pampo(Pam3-CSKKKK (SEQ. ID. NO: 2) 25 μg + Poly(I:C) 20 μg) + recombinant JEV gE antigen 0.1 μg |
| G5 | L-Pampo(Pam3-CSKKKK (SEQ. ID. NO: 2) 25 μg + Poly(I:C) 20 μg) + recombinant JEV gE antigen 0.5 μg |
| G6 | Lipo-pam(DC-Chol:DOPE(3:7) 125 μg + Pam3-CSKKKK (SEQ. ID. NO: 2) 25 μg) + Poly(I:C) 40 μg + recombinant JEV gE antigen 0.1 μg |
| G7 | Lipo-pam(DC-Chol:DOPE(3:7) 125 μg + Pam3-CSKKKK (SEQ. ID. NO: 2) 25 μg) + Poly(I:C) 40 μg + recombinant JEV gE antigen 0.5 μg |

<12-2> Analysis of Humoral Immune Response

In order to analyze the humoral immune response induced by the test vaccine administered in Example <12-1>, samples were prepared by separating the sera of mice at week 0 before immunization, week 2, 2 weeks after the first vaccination and week 4, 2 weeks after the second vaccination. The total IgG antibody titer against the JEV gE antigen was analyzed using the prepared samples by the same manner as described in Example <2-2> except that the recombinant JEV gE antigen or inactivated JEV antigen was coated on a 96-well microplate at the concentration of 100 ng/well.

As a result, as shown in FIGS. 24A and 24B, the total IgG antibody titer against the recombinant JEV gE antigen (FIG. 24A) and the total IgG antibody titer against the inactivated JEV antigen (FIG. 24B) were highest in the G7 group using the Lipo-pam formulation (G7 group) with 0.5 μg/dose of antigen. As a result of isotype analysis of antibody against the recombinant JEV gE antigen, the IgG1 type antibody titer was highest in the G5 group using L-pampo, and the antibody titers of IgG2a and IgG2b types were highest in the G7 group using Lipo-pam.

<12-3> Analysis of Cell-Mediated Immune Response

In order to analyze the cell-mediated immune response induced by the test vaccine administered in Example <12-1>, whole splenocytes were isolated by extracting the spleens from the mice at week 4, 2 weeks after the $2^{nd}$ vaccination. Then, the cell-mediated immune response was analyzed by ELISPOT assay and cytokine ELISA by the same manner as described in Example <2-3> except that the recombinant JEV gE antigen or inactivated JEV antigen was used.

As a result, as shown in FIG. 25A, according to the results of ELISPOT of IFN-γ and IL-4, IFN-γ and IL-4 were most produced in the G6 and G7 groups using Lipo-pam (FIG. 25A).

As shown in FIG. 25B, according to the results of cytokine ELISA, IFN-γ, IL-4 and TNF-α were secreted in the order by Lipo-pam formulation (G6 and G7 groups), L-pampo formulation (G4 and G5 groups) and inactivated vaccine (G2 and G3 groups) (FIG. 25B).

Therefore, it was confirmed from the results of <Example 12> that the use of an immunoactive substance with Lipo-pam in the preparation of the recombinant Japanese encephalitis vaccine improved the vaccine efficacy by inducing humoral and cell-mediated immune responses. This suggests that Lipo-pam has immune-enhancing effects on various antigens.

Example 13. Comparison of Immunogenicity of Vaccine Formulated with Alum, L-Pampo or Lipo-Pam Against Seasonal Inactivated Influenza Virus Antigen The immunogenicity of the vaccine formulated with alum, L-pampo or Lipo-pam was compared using seasonal inactivated influenza virus antigen.

<13-1> Preparation and Administration of Test Vaccine

Lipo-Pam was prepared by the same manner as described in Example <2-1> except that DC-Chol, DOPE, DPPC and Pam3-CSKKKK (SEQ. ID. NO: 2) were dissolved, and DC-Chol, DOPE, DPPC and Pam3-CSKKKK (SEQ. ID. NO: 2) were mixed so that the concentration of lipids (DC-Chol:DOPE=3:7 or DC-Chol:DOPE=1:1) was 125 μg/dose, and the concentration of Pam3-CSKKKK (SEQ. ID. NO: 2) was 25 μg/dose. L-pampo was prepared by mixing 25 μg/dose of Pam3-CSKKKK (SEQ. ID. NO: 2), 20 μg/dose of Poly(I:C), and 0.5 μg/dose of seasonal inactivated influenza virus antigens of 4 strains. The seasonal inactivated influenza virus antigens of 4 strains were obtained from A/California/07/2009 (H1N1), A/Hong Kong/4801/2014 (H3N2), B/Phuket/3073/2013 (BY) and B/Brisbane/60/2008 (BV). These antigens were amplified in eggs, produced, and purified. Then, test vaccines were prepared by mixing Lipo-Pam with Poly(I:C) at the concentration of 40 μg/dose and adding the seasonal inactivated influenza virus antigen thereto at the concentration of 0.5 μg/dose. The prepared vaccines were injected intramuscularly to 6 week old C57BL/6 female mice (Orient Bio Inc., Korea) twice at two-week intervals.

TABLE 13

Preparation conditions of test vaccines for each test group

| Test Group | Composition |
|---|---|
| G1 | PBS |
| G2 | seasonal inactivated influenza virus antigen 0.5 μg/strain |
| G3 | alum + seasonal inactivated influenza virus antigen 0.5 μg/strain |
| G4 | L-Pampo(Pam3-CSKKKK (SEQ. ID. NO: 2) 25 μg + Poly(I:C) 20 μg) + seasonal inactivated influenza virus antigen 0.5 μg/strain |
| G5 | Lipo-pam(DC-Chol:DOPE(3:7) 125 μg + Pam3-CSKKKK (SEQ. ID. NO: 2) 25 μg) + Poly(I:C) 40 μg + seasonal inactivated influenza virus antigen 0.5 μg/strain |
| G6 | Lipo-pam(DC-Chol:DPPC(1:1) 125 μg + Pam3-CSKKKK (SEQ. ID. NO: 2) 25 μg) + Poly(I:C) 40 μg + seasonal inactivated influenza virus antigen 0.5 μg/strain |

<13-2> Analysis of Humoral Immune Response

In order to analyze the humoral immune response induced by the test vaccine administered in Example <13-1>, samples were prepared by separating the sera of mice at week 0 before immunization, week 2, 2 weeks after the first vaccination and week 4, 2 weeks after the second vaccination. The total IgG antibody titer against the seasonal inactivated influenza virus antigen was analyzed using the prepared samples by the same manner as described in Example <2-2> except that the seasonal inactivated influenza virus antigens of 4 strains were coated in 96-well microplates at the concentration of 25 ng/well, respectively.

As a result, as shown in FIG. 26, the total IgG antibody titer against the seasonal inactivated influenza virus antigen was the highest in the G4 group (L-pampo formulation) in all 4 strains and was also excellent in the G5 and G6 groups (Lipo-pam formulation). In particular, the high IgG antibody titer was observed in the G6 group (DC-Chol:DPPC=1:1). On the other hand, the total IgG antibody titer in the G2 group administered with antigen alone and the G3 group using alum as an immune-enhancing agent was significantly lower than in the test group using Lipo-pam formulation (FIG. 26).

<13-3> Analysis of Cell-Mediated Immune Response

In order to analyze the cell-mediated immune response induced by the test vaccine administered in Example <13-1>, whole splenocytes were isolated by extracting the spleens from the mice at week 4, 2 weeks after the $2^{nd}$ vaccination. Then, the cell-mediated immune response was analyzed by ELISPOT assay and cytokine ELISA by the same manner as described in Example <2-3> except that the seasonal inactivated influenza virus antigens of 4 strains were used.

As a result, as shown in FIG. 27, according to the results of ELISPOT of IFN-γ, IFN-γ was the most produced against the seasonal inactivated influenza virus antigens of 4 strains in the G5 and G6 groups (Lipo-pam formulation) (FIG. 27). As shown in FIG. 28, according to the results of ELISPOT of IL-4, IL-4 was also secreted in the G5 and G6 groups (Lipo-pam formulation), which was lower than in the G2 group administered with antigen alone and the G3 group added with alum (FIG. 28).

As shown in FIGS. 29 to 31, according to the results of cytokine ELISA, lots of IFN-γ and TNF-α were produced in the G5 and G6 groups (Lipo-pam formulation) (FIGS. 29 and 30). IL-4 was also secreted in the G5 and G6 groups, which was lower than in the G2 group administered with antigen alone and the G3 group added with alum (FIG. 31).

Therefore, it was confirmed from the results of <Example 13> that the use of Lipo-pam as an adjuvant in the preparation of the seasonal inactivated influenza virus vaccine improved the vaccine efficacy by inducing humoral and cell-mediated immune responses. From the above, it was also confirmed that the vaccine adjuvant Lipo-pam according to the present invention can be used with various kinds of antigens without any limitation in the type of antigen.

What is claimed is:

1. A vaccine adjuvant, comprising:
a liposome having a lipid bilayer;
a lipopeptide inserted into the lipid bilayer; and
an immunoactive substance, as an active ingredient, mixed with the liposome, wherein, the lipopeptide is any one or more selected from the group consisting of:
Pam3-CSKKKK, wherein amino acids sequence CSKKKK is according to SEQ ID NO:2,
PHC-SKKKK, wherein amino acids sequence SKKKK is according to SEQ ID NO:3,
Pam2Cys-SKKKK, wherein amino acids sequence SKKKK is according to SEQ ID NO:3,
PamDhc-SKKKK, wherein amino acids sequence SKKKK is according to SEQ ID NO:3,
Pam-CSKKKK, wherein amino acids sequence CSKKKK is according to SEQ ID NO:2,
Dhc-SKKKK, wherein amino acids sequence SKKKK is according to SEQ ID NO:3, and
Pam2CGDPKHPKSF, wherein amino acids sequence CGDPKHPKSF is according to SEQ ID NO:4, and
wherein the immunoactive substance is any one or more selected from the group consisting of Poly(I:C) and QS21.

2. The vaccine adjuvant according to claim 1, wherein the lipid bilayer comprises one or more lipids selected from the group consisting of DOTAP (1,2-Dioleoyl-3-Trimethylammonium-Propane), DOPE (1,2-dioleoyl-sn-glycero-3-phosphoethanolamine), DDA (Dimethyldioctadecylammonium), DC-chol (3β-[N—(N′,N-Dimethylaminoethane)-carbamoyl]cholesterol), DOPG (1,2-Dioleoyl-sn-Glycero-3-[Phospho-rac-(1-glycerol)]), DPPC (1,2-dipalmitoyl-sn-glycero-3-phosphocholine), DOPC (1,2-dioleoyl-sn-glycero-3-phosphocholine) and cholesterol.

3. The vaccine adjuvant according to claim 1, wherein the Poly(I:C) is 50 to 5,000 bp in length.

4. A vaccine composition comprising the vaccine adjuvant of claim 1 and an antigen.

5. The vaccine composition according to claim 4, wherein the antigen is a protein of a pathogen, a recombinant protein, a glycoprotein, a peptide, a polysaccharide, a lipopolysaccharide or a polynucleotide.

6. The vaccine composition according to claim 4, wherein the antigen is derived from cells or viruses.

7. The vaccine composition according to claim 4, wherein the antigen is any one or more selected from the group consisting of Varicella-Zoster Virus gE (glycoprotein E) antigen, Japanese encephalitis virus gE (glycoprotein E) antigen and seasonal inactivated influenza virus antigen.

8. The vaccine composition according to claim 4, wherein the vaccine induces cell-mediated immune response.

9. The vaccine composition according to claim 4, wherein the vaccine induces Th1 immune response.

10. A vaccine adjuvant, comprising:
(i) a liposome having:
(a) a lipid bilayer formed of one or more lipids selected from the group consisting of DOTAP (1,2-Dioleoyl-3-Trimethylammonium-Propane), DOPE (1,2-dioleoyl-sn-glycero-3-phosphoethanolamine), DDA (Dimethyldioctadecylammonium), DC-chol (3β-[N—(N′,N-Dimethylaminoethane)-carbamoyl]cholesterol), DOPG (1,2-Dioleoyl-sn-Glycero-3-[Phospho-rac-(1-glycerol)]), DPPC (1,2-dipalmitoyl-sn-glycero-3-phosphocholine), DOPC (1,2-dioleoyl-sn-glycero-3-phosphocholine) and cholesterol; and
(b) a lipopeptide inserted into the lipid bilayer, wherein, the lipopeptide is any one or more selected from the group consisting of Pam3-CSKKKK, wherein amino acids sequence CSKKKK is according to SEQ ID NO:2, PHC-SKKKK, wherein amino acids sequence SKKKK is according to SEQ ID NO:3, Pam2Cys-SKKKK, wherein amino acids sequence SKKKK is according to SEQ ID NO:3, PamDhc-SKKKK, wherein amino acids sequence SKKKK is according to SEQ ID NO:3, Pam-CSKKKK, wherein amino acids sequence CSKKKK is according to SEQ ID NO:2, Dhc-SKKKK, wherein amino acids sequence SKKKK is according to SEQ ID NO:3, and Pam2CGDPKHPKSF, wherein amino acids sequence CGDPKHPKSF is according to SEQ ID NO:4; and
(ii) an immunoactive substance, as an active ingredient, mixed with the liposome, wherein the immunoactive substance is any one or more selected from the group consisting of Poly(I:C) and QS21.

11. The vaccine adjuvant according to claim 10, wherein the Poly(I:C) is 50 to 5,000 bp in length.

12. A vaccine composition comprising the vaccine adjuvant of claim 10 and an antigen.

13. The vaccine composition according to claim 12, wherein the antigen is a protein of a pathogen, a recombinant protein, a glycoprotein, a peptide, a polysaccharide, a lipopolysaccharide or a polynucleotide.

14. The vaccine composition according to claim 12, wherein the antigen is any one or more selected from the group consisting of Varicella-Zoster Virus gE (glycoprotein E) antigen, Japanese encephalitis virus gE (glycoprotein E) antigen and seasonal inactivated influenza vim s antigen.

15. The vaccine adjuvant according to claim 10, wherein the lipopeptide inserted into the lipid bilayer is present at a concentration of 20 to 2500 μg/dose of the vaccine adjuvant.

16. The vaccine adjuvant according to claim 1, wherein the lipopeptide inserted into the lipid bilayer is present at a concentration of 20 to 2500 μg/dose of the vaccine adjuvant.

17. The vaccine adjuvant according to claim 10, wherein the one or more lipids is included in the liposome at a concentration of 15 to 3000 μg/dose of the vaccine adjuvant.

18. The vaccine adjuvant according to claim 10, wherein the immunoactive substance is included at a concentration of 10 to 1500 μg/dose of the vaccine adjuvant.

19. The vaccine adjuvant according to claim 2, wherein the one or more lipids is included in the liposome at a concentration of 15 to 3000 μg/dose of the vaccine adjuvant.

20. The vaccine adjuvant according to claim 10, wherein the immunoactive substance is included at a concentration of 10 to 1500 μg/dose of the vaccine adjuvant.

* * * * *

```
                        SEQUENCE LISTING

<160> NUMBER OF SEQ ID NOS: 4

<210> SEQ ID NO 1
<211> LENGTH: 1656
<212> TYPE: DNA
<213> ORGANISM: Artificial Sequence
<220> FEATURE:
<223> OTHER INFORMATION: glycoprotein E of Varicella-Zoster Virus

<400> SEQUENCE: 1
ctagccacca tggggacagt aaacaaacct gtggtgggcg tgctaatggg gttcggaatt      60
atcacgggta cgctgaggat aacgaatccg gtcagagcat ccgtcttgcg atacgatgat     120
tttcataccg acgaagacaa gctggataca aactccgttt acgagcctta ctaccactcc     180
gatcacgccg agtctagctg ggtcaatcgt ggcgagtctt cacgaaaagc gtacgatcat     240
aactcacctt atatttggcc ccgtaatgac tatgacggat ttttggagaa cgcacacgaa     300
caccatgggg tgtataatca gggcaggggt atcgatagcg gggaacggct tatgcagccc     360
acacagatgt ctgcacagga ggaccttggg gacgatacgg gcatccacgt tatccctacg     420
ctgaacggcg atgacagaca taagattgta aatgtggacc aaaggcagta cggtgacgtg     480
ttcaaaggag atcttaatcc aaaaccgcag ggccagagac tcatagaggt gtcagtggaa     540
gagaatcacc cttttactct gcgcgcacct attcagcgga tctatggagt ccgctacact     600
```

```
gagacttgga gcttcctgcc gtcactgacc tgcactggtg acgctgcccc tgccatccag    660
cacatatgtc tgaaacacac aacatgcttc caagacgtgg tggtggacgt ggattgcgca    720
gagaacacta agaagatca gttggccgag atcagttaca ggtttcaagg caagaaggaa    780
gctgaccaac catggattgt tgtaaacacc agcacactgt ttgacgagct cgaactcgac    840
ccccccgaga tcgaacctgg tgtcttgaag gtactgcgga cagaaaagca gtacttgggt    900
gtgtacattt ggaacatgcg cggctcagat ggtacgtcta cctacgccac gttttttggtt    960 acctggaagg gggacgagaa aacaagaaac cctacgcccg cagttacgcc tcagccaaga   1020
ggggctgagt ttcatatgtg gaattatcac tcgcacgtct tttcagttgg cgatacgttc   1080
tccttggcca tgcacctcca gtataagata cacgaagcac cattcgactt gctgttagag   1140
tggttgtatg tccccattga tcctacttgc cagccaatgc ggctgtatag cacttgtctc   1200
tatcatccca atgctcccca gtgcctctct cacatgaatt ccggttgcac attcacctcc   1260
ccacatttag cccagcgcgt tgcaagcaca gtgtatcaaa attgtgagca tgcagataac   1320
tacaccgctt attgtctggg catctctcat atggagccta gttttggcct aatcctccat   1380
gacgggggca ccacgctgaa gttcgtggat acaccagagt ctttgtctgg attatacgtt   1440
tttgtcgtgt atttcaacgg acacgttgaa gccgtggcat acactgtcgt atccacagtc   1500
gaccatttcg taaacgccat cgaagagcgt ggattcccac caacagccgg ccagccacca   1560
gcgactacca agcccaagga aattacccccc gtcaaccccg gaacttcacc acttctacga   1620
tatgccgcat ggaccggagg ccttgcttga ctcgag                             1656
```

<210> SEQ ID NO 2
<211> LENGTH: 6
<212> TYPE: PRT
<213> ORGANISM: Artificial Sequence
<220> FEATURE:
<223> OTHER INFORMATION: amino acids of lipopetide adjuvants Pam3-CSKKKK
      and Pam-CSKKKK

<400> SEQUENCE: 2

Cys Ser Lys Lys Lys Lys
1               5

<210> SEQ ID NO 3
<211> LENGTH: 5
<212> TYPE: PRT
<213> ORGANISM: Artificial Sequence
<220> FEATURE:
<223> OTHER INFORMATION: amino acids of lipopetide adjuvants PHC-SKKKK,
      Pam2Cys-SKKKK, Pamdhc-SKKKK, and Dhc-SKKKK

<400> SEQUENCE: 3

Ser Lys Lys Lys Lys
1               5

<210> SEQ ID NO 4
<211> LENGTH: 10
<212> TYPE: PRT
<213> ORGANISM: Artificial Sequence
<220> FEATURE:
<223> OTHER INFORMATION: amino acids of lipopetide adjuvant
      FSL-1(Pam2CGDPKHPKSF)

<400> SEQUENCE: 4

Cys Gly Asp Pro Lys His Pro Lys Ser Phe
1               5                   10